United States Patent
Al-Huwaider et al.

(10) Patent No.: US 11,661,844 B2
(45) Date of Patent: May 30, 2023

(54) METHOD AND APPARATUS FOR FLUID CHARACTERIZATION AND HOLDUP ESTIMATION USING ACOUSTIC WAVES

(71) Applicant: Saudi Arabian Oil Company, Dhahran (SA)

(72) Inventors: Mustafa A. Al-Huwaider, Dhahran (SA); Shouxiang Mark Ma, Dhahran (SA); Nader H. Hwety, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 105 days.

(21) Appl. No.: 17/065,005

(22) Filed: Oct. 7, 2020

(65) Prior Publication Data
US 2022/0106878 A1    Apr. 7, 2022

(51) Int. Cl.
*E21B 49/08*    (2006.01)
*G06F 30/20*    (2020.01)
(Continued)

(52) U.S. Cl.
CPC .......... *E21B 49/0875* (2020.05); *G01F 1/66* (2013.01); *G01N 9/00* (2013.01); *G01N 33/18* (2013.01); *G01N 33/2823* (2013.01); *G01V 1/46* (2013.01); *G01V 1/50* (2013.01); *G06F 30/20* (2020.01); *E21B 2200/20* (2020.05); *G01V 2210/1299* (2013.01); *G01V 2210/1429* (2013.01); *G01V 2210/663* (2013.01)

(58) Field of Classification Search
CPC .. G06F 1/66; G06F 30/20; G01N 9/00; G01N 33/18; G01N 33/2823; G01V 1/46; G01V 1/50; E21B 49/0875
See application file for complete search history.

(56) References Cited

U.S. PATENT DOCUMENTS 3,603,145 A    9/1971   Morris
5,367,911 A    11/1994  Jewell et al.
(Continued)

OTHER PUBLICATIONS

Bauldauff et al., "Profiling and quantifying complex multiphase flow," Oilfield Review, Autumn 2004, 10 pages.
(Continued)

*Primary Examiner* — John Fitzgerald
(74) *Attorney, Agent, or Firm* — Fish & Richardson P.C.

(57) ABSTRACT

Systems and methods include a computer-implemented method for predicting fluid holdups along the borehole or the pipe on surface and to perform fluid typing and fluid properties characterization. Acoustic waves are transmitted by an array of acoustic wave transducers. Each transducer is configured to transmit acoustic waves at a different frequency. The acoustic waves are received by an array of acoustic wave receivers fixed on the bow centralizer on the tool used in the borehole. Each receiver is configured to receive only the given frequency of a given transducer, forming a receiver-transducer pair for the given frequency. Acoustic speeds measured at each given frequency and analyzed. A model is generated based on the analyzing. The model is configured to predict fluid holdups across the borehole and to perform fluid typing and fluid properties characterization in one phase, two phase, and three phase applications of gas, oil, and water.

20 Claims, 16 Drawing Sheets

(51) Int. Cl.
  G01F 1/66 (2022.01)
  G01N 9/00 (2006.01)
  G01N 33/18 (2006.01)
  G01N 33/28 (2006.01)
  G01V 1/46 (2006.01)
  G01V 1/50 (2006.01)

(56) References Cited

U.S. PATENT DOCUMENTS

| | | | | |
|---|---|---|---|---|
| 5,531,112 | A * | 7/1996 | Young | G01N 33/2823 166/117.7 |
| 5,631,413 | A * | 5/1997 | Young | E21B 47/103 73/61.49 |
| 6,176,129 | B1 * | 1/2001 | Aguesse | E21B 47/01 73/152.29 |
| 7,069,775 | B2 * | 7/2006 | Fredette | E21B 47/085 73/152.17 |
| 7,603,236 | B2 * | 10/2009 | North | E21B 47/10 702/6 |
| 7,975,541 | B2 * | 7/2011 | Large | E21B 17/1021 166/241.5 |
| 10,294,771 | B2 * | 5/2019 | Donzier | E21B 47/10 |
| 10,316,648 | B2 | 6/2019 | Swett | |
| 11,460,443 | B2 * | 10/2022 | Al-Huwaider | E21B 49/0875 |
| 2016/0326866 | A1 | 10/2016 | Swett | |
| 2020/0208514 | A1 * | 7/2020 | Swett | G01F 1/69 |
| 2020/0208515 | A1 | 7/2020 | Swett et al. | |
| 2020/0362645 | A1 * | 11/2020 | Donzier | E21B 49/082 |
| 2022/0260530 | A1 * | 8/2022 | Al-Huwaider | G01F 1/002 |

OTHER PUBLICATIONS

Liu, "Acoustic Properties of Reservoir Fluids," A dissertation submitted to the Department of Geophysics and the Committee on Graduate Studies, Stanford University, Jun. 1998, 111 pages.

McCoy et al., "Analyzing Well Performance 98," Southwestern Petroleum Short Course, 1973, 9 pages.

Moses, "Geothermal Gradients," Drilling & Production Practice, Core Lab. Inc., Dallas, Texas, 1961, 7 pages.

oilproduction.net [online], "Acoustic Velocity for Natural Gas," retrieved on Jan. 7, 2021, URL <http://oilproduction.net/files/Acoustic%20Velocity%20for%20Natural%20Gas.pdf>, 6 pages.

Proactive Diagnostic Services, "Multiple—Array Production Suite (MAPS)," 2017, 2 pages.

Thomas et al., "Determination of Acoustic Velocities for Natural Gas," SPE 2579, Journal of Petroleum Technology, Jul. 1970, 22(7):889-895.

Wang et al., "Acoustic Velocities in Petroleum Oils," SPE 18163, presented at the SPE Annual Technical Conference and Exhibition, Houston, Texas, Oct. 2-5, 1988, 6 pages.

PCT International Search Report and Written Opinion in International Appln. No. PCT/US2021/053740, dated Feb. 1, 2022, 13 pages.

\* cited by examiner

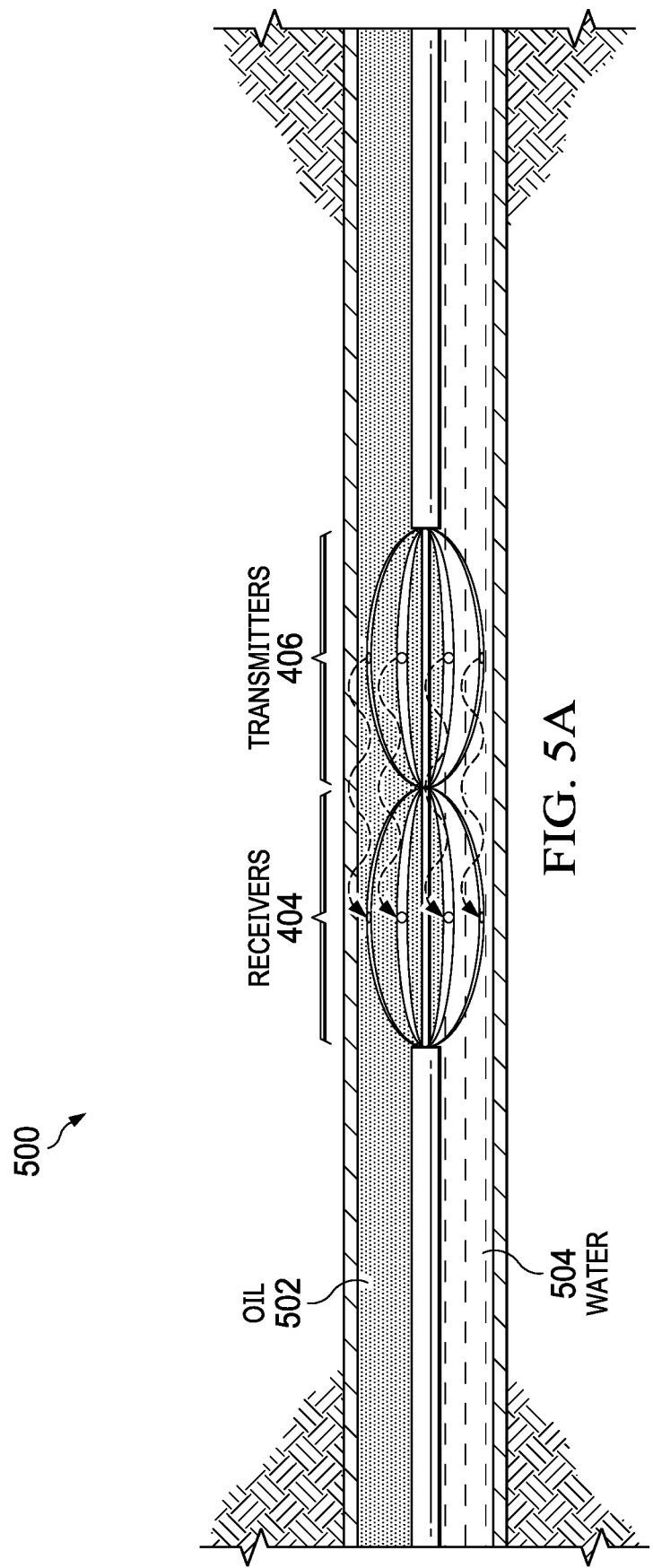

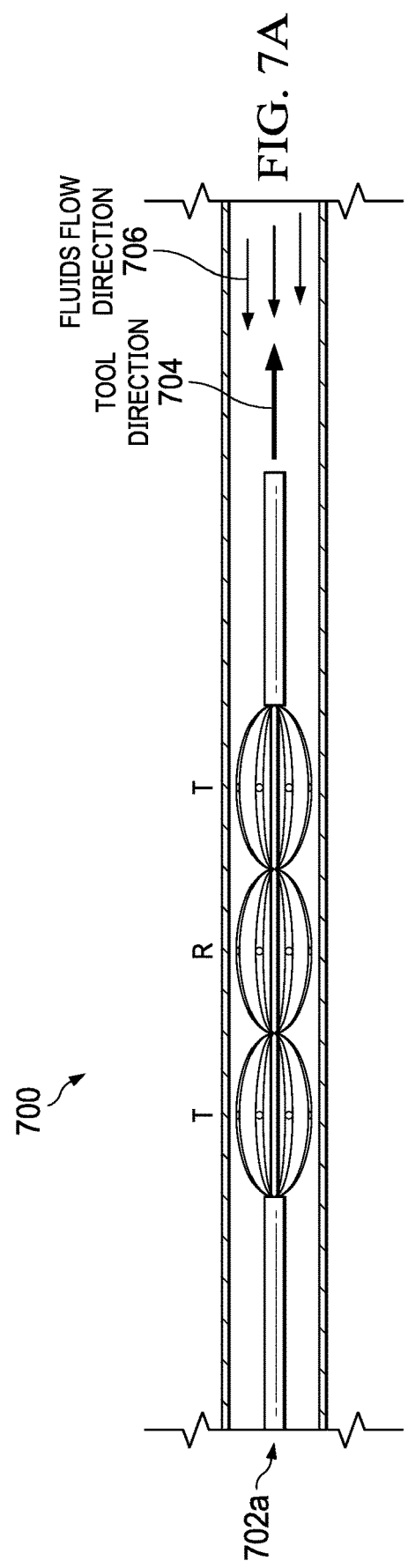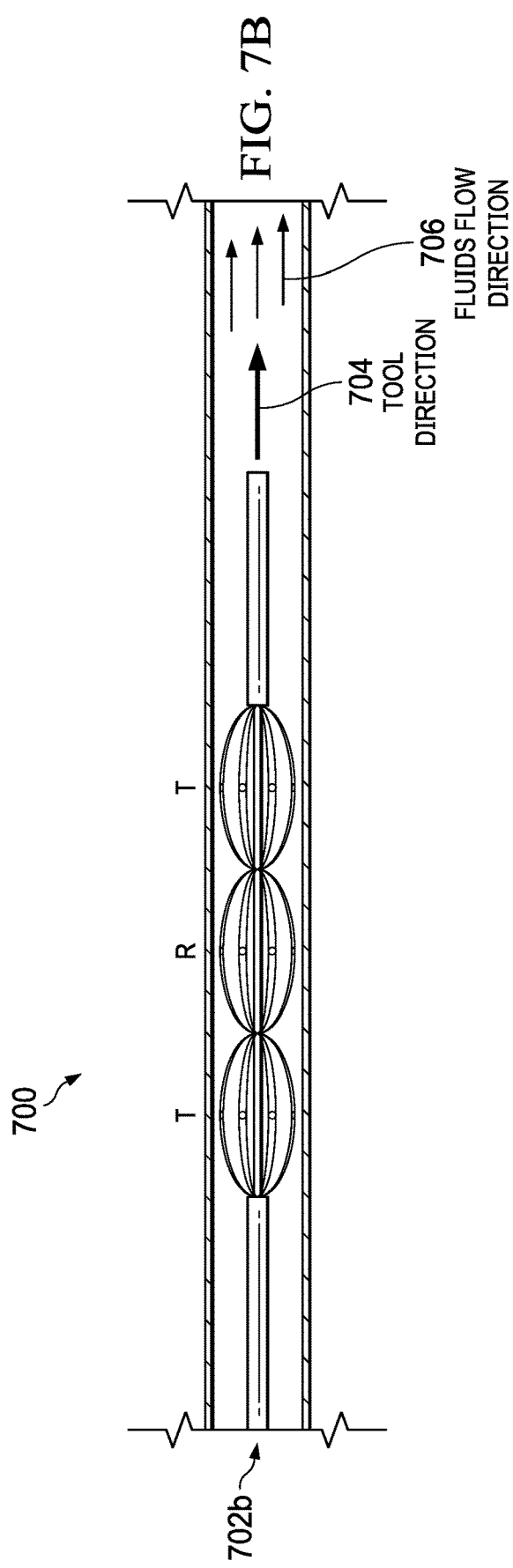

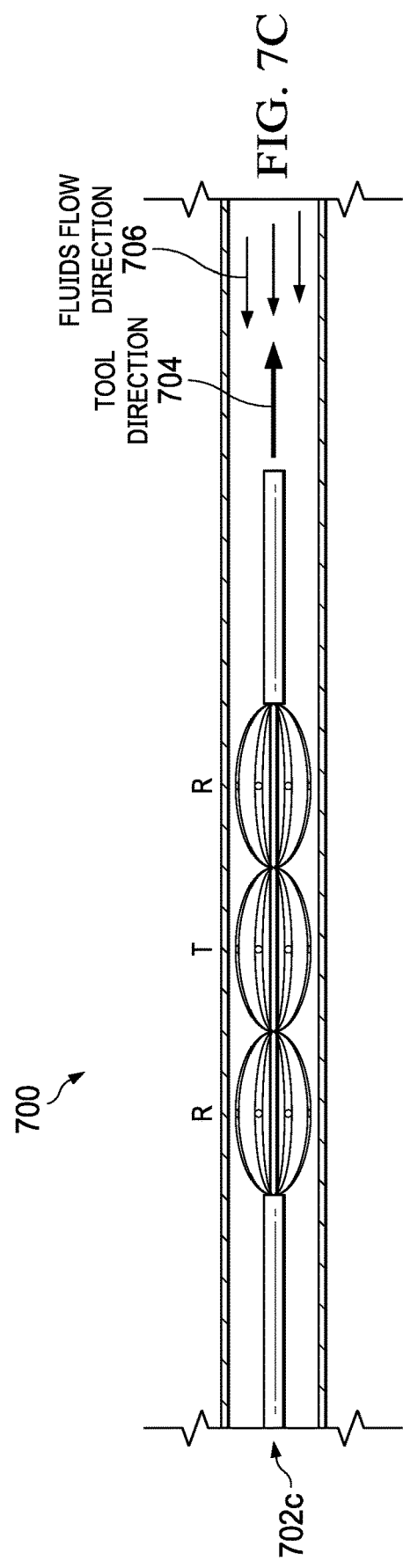
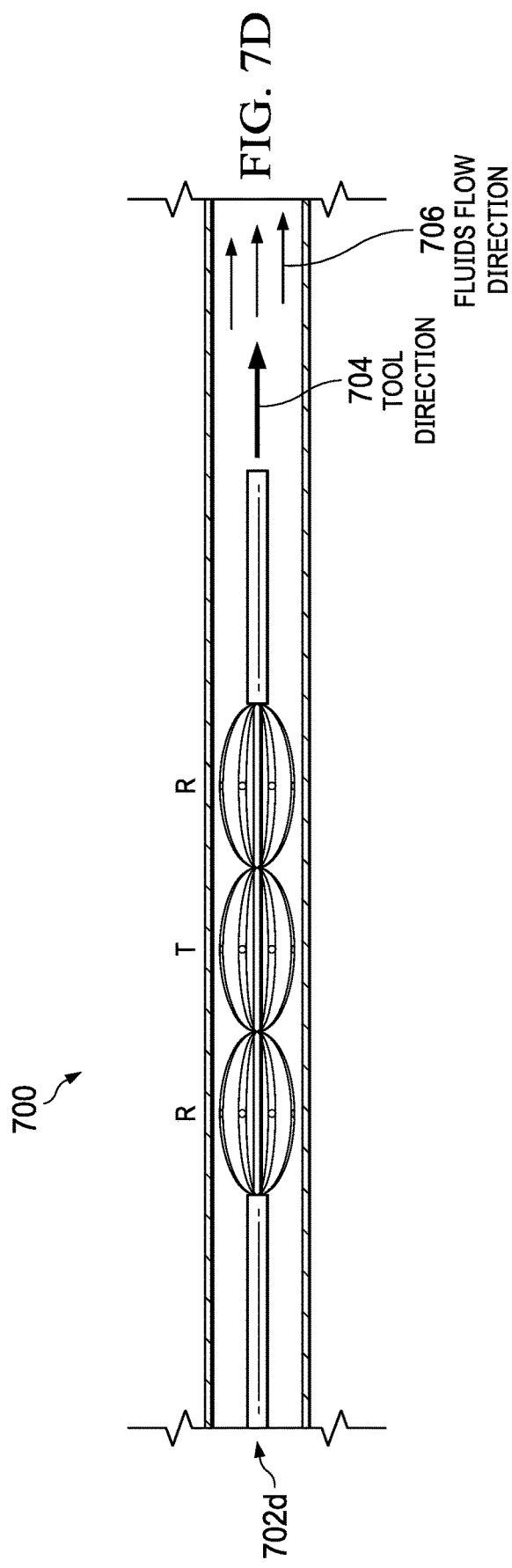

METHOD AND APPARATUS FOR FLUID CHARACTERIZATION AND HOLDUP ESTIMATION USING ACOUSTIC WAVES

BACKGROUND

The present disclosure applies to using transmitters (transducers) and receivers to help in predicting fluids' holdup along a borehole.

Conventional systems may expose a portion of wellbore fluid to a range of acoustic frequencies to measure electrical admittance. Some conventional systems use acoustic measurements for wellbore reservoir fluids characterization and holdup estimation. Conventional systems may force a portion of a mixed fluid to pass through a cavity in order to do measurements. Such conventional systems may provide a one-point measurement, applicable for homogenous flows such as in vertical wells.

SUMMARY

The present disclosure describes techniques for using an array of probes (including transducers and receivers) that are used on bow centralizers to predict fluids' holdup along the borehole. For example, the techniques can include the use of acoustic waves to estimate fluid type and holdup.

In some implementations, a computer-implemented method includes the following. Acoustic waves are transmitted by an array of acoustic wave transducers fixed on a bow centralizer on a tool used in a borehole. Each transducer in the array of acoustic wave transducers is configured to transmit acoustic waves at a given frequency different from frequencies of other transducers in the array of acoustic wave transducers. The acoustic waves are received by an array of acoustic wave receivers fixed on the bow centralizer on the tool used in the borehole. Each receiver in the array of acoustic wave receivers is configured to receive only the given frequency of a given transducer, forming a receiver-transducer pair for the given frequency. Acoustic speeds measured at each given frequency are analyzed. A model is generated based on the analyzing. The model is configured to predict fluid holdups along the borehole and to perform fluid typing and fluid properties characterization in one phase, two phase, and three phase applications of gas, oil, and water.

The previously described implementation is implementable using a computer-implemented method; a non-transitory, computer-readable medium storing computer-readable instructions to perform the computer-implemented method; and a computer-implemented system including a computer memory interoperably coupled with a hardware processor configured to perform the computer-implemented method the instructions stored on the non-transitory, computer-readable medium.

The subject matter described in this specification can be implemented in particular implementations, so as to realize one or more of the following advantages. First, acoustic waves can be used to estimate fluid type and holdup in real time, providing a time-saving and timeliness advantage over techniques that are currently being used in production logging. The term real-time can correspond to events that occur within a specified period of time, such as within a few minutes or seconds. Second, the techniques can improve gas entry detection, gas quantification, and water salinity estimation and emulsion identification.

The details of one or more implementations of the subject matter of this specification are set forth in the Detailed Description, the accompanying drawings, and the claims. Other features, aspects, and advantages of the subject matter will become apparent from the Detailed Description, the claims, and the accompanying drawings.

DESCRIPTION OF DRAWINGS

FIG. 5A is a diagram showing an example of the use of an acoustic fluid holdup tool in an oil-water two phase, according to some implementations of the present disclosure.

FIGS. 7A-7D are diagrams showing examples of symmetrical compensated acoustic logging tools at different transmitter/receiver arrangements and in different fluid flow directions, according to some implementations of the present disclosure.

Like reference numbers and designations in the various drawings indicate like elements.

DETAILED DESCRIPTION

Figure 1:
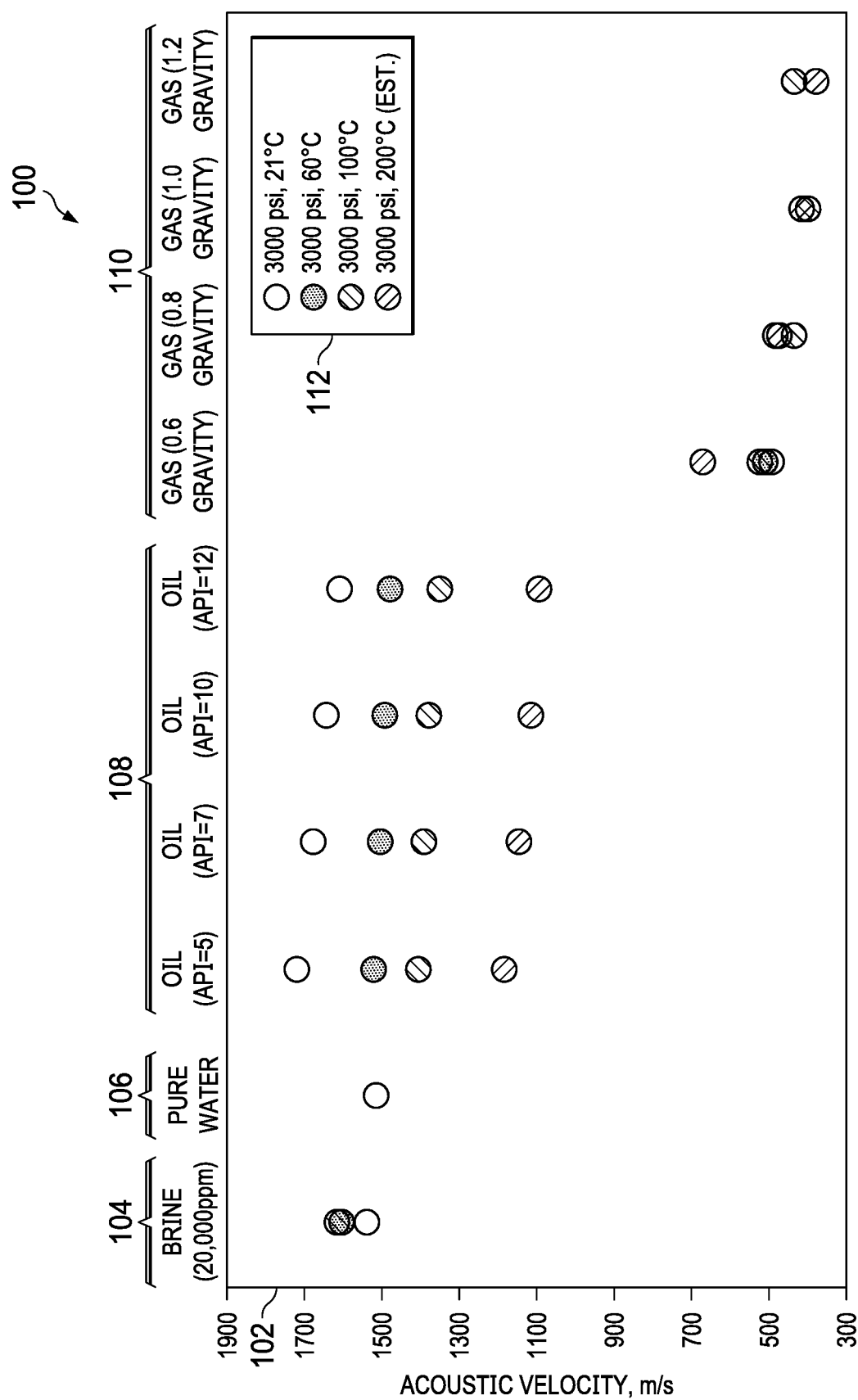
FIG. 1 is a graph showing example plots of acoustic speeds through different materials, according to some implementations of the present disclosure.

The following detailed description describes techniques for using an array of probes (including transducers and receivers) fixed on bow centralizers to predict fluids' holdup along the borehole or pipe on surface. For example, the techniques can include using acoustic waves to estimate fluid type and holdup (for example, water-oil holdup), and to estimate emulsions and water salinity. Production logging spinners can be combined with a series of non-acoustic sensors such as electric, optical, and capacitance probes to provide fluid holdup data for phase flow rate calculations. In addition, arrays of sensors can be deployed in horizontal well sections or surface pipes transporting fluids.

Conventional systems that force a portion of a mixed fluid to pass through a cavity typically fail to represent multiphase fluids separated by gravity in horizontal sections. The one-point measurement provided by such conventional systems may be applicable for homogenous flows such as bubble flow in vertical wells, but not in stratified flows in highly-deviated and horizontal wells or pipes. The current disclosure describes techniques for using an array of probes (including transducers and receivers) that are fixed on bow centralizers. The techniques can be used to predict fluids holdup along the borehole or pipe. The predictions can complement information from array production logs obtained using an array of spinners and other non-acoustic holdup sensors. The combination of predictions and logs can help in estimating the flow rate of each fluid type. The techniques can also be used in fluid typing and fluid properties characterization.

Conventional acoustic systems may expose a portion of wellbore fluid to a range of acoustic frequencies to measure electrical admittance. The current disclosure describes techniques for providing an array of transducers, where each transducer has a different frequency, which avoids frequency interference. Each transducer can be paired with an opposing receiver to measure acoustic speed. Fluid type, density, and water salinity can be estimated for each fluid type with known acoustic speed of fluids at specific pressure (P), temperature (T), and salinity for water.

Conventional systems may also fail to estimate emulsion between different fluids in horizontal sections. The current disclosure describes techniques for predicting and identifying emulsions.

Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and inasmuch as such details are within the skill of one of ordinary skill in the art. The present disclosure is not intended to be limited to the described or illustrated implementations, but to be accorded the widest scope consistent with the described principles and features.

The addition of an array of acoustic probes can improve the quality of the integrated data interpretation and overcome some challenges such as emulsion estimation. Further, the addition of an array of acoustic probes can also help in predicting fluid properties, such as the density of oil and gas, and the salinity of water from each contributing layer of the reservoir.

Figure 2:
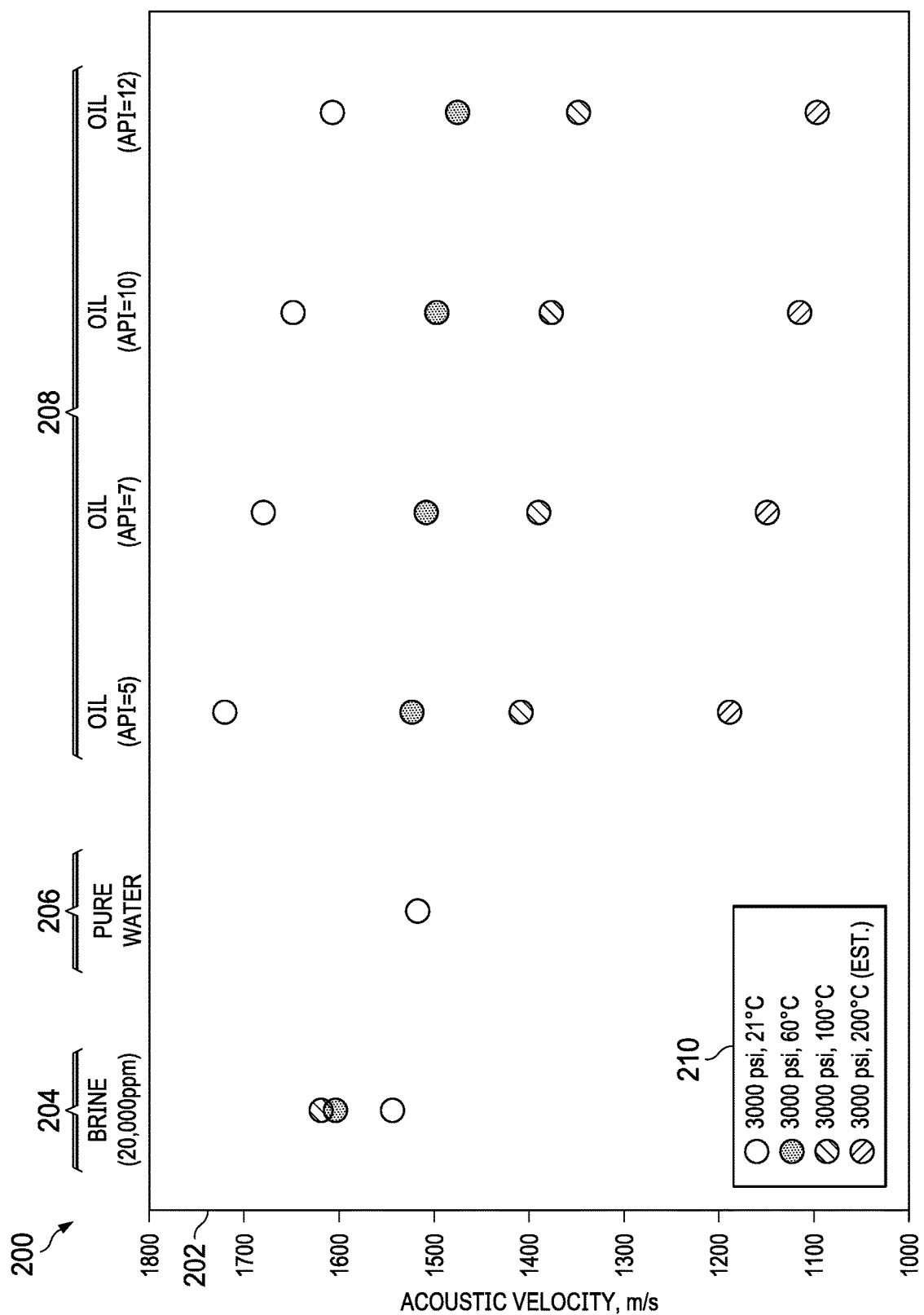
FIG. 2 is a graph showing examples of plots of acoustic speeds in a liquid hydrocarbon fluid and water, according to some implementations of the present disclosure.
Figure 3:
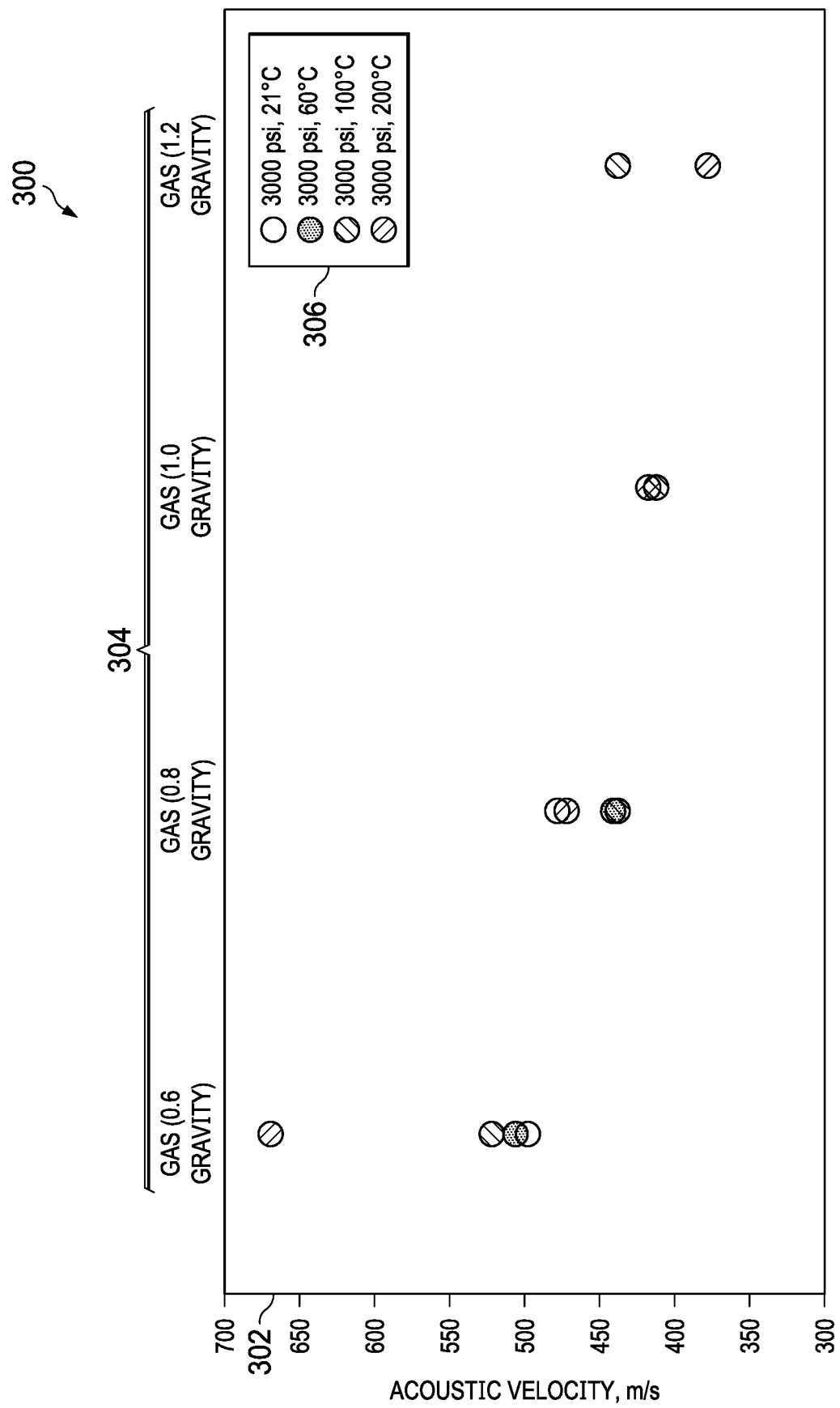
FIG. 3 is a graph showing examples of plots of acoustic speeds in a hydrocarbon gas, according to some implementations of the present disclosure.

Acoustic waves travel through different materials at different speeds, depending on each material's density and stiffness. Generally, acoustic waves travel faster in solids than in liquids, and faster in liquids than in gases. The differences in travel speeds exist because solids are more difficult to compress than liquids, while liquids are more difficult to compress than gases. Additionally, other factors, such as pressure and temperature, can significantly impact acoustic velocity. The effect can depend on the material type. For example, in hydrocarbon fluid (or oil), acoustic velocities increase as pressure or molecular weight/density (for example, determined by American Petroleum Institute (API) gravity) increases. Also, acoustic velocities decrease as temperature increases. In water, however, a greater temperature, pressure, or salinity produces a greater velocity. Temperature increases weaken an un-bonded structure, such as oil molecules, which in turn slows acoustic velocity through the un-bonded structure. FIGS. 1-3 show differences in acoustic velocity in different types of oils, gases, and waters at constant pressure of 3000 pounds per square inch (psi) at varying temperatures.

FIG. 1 is a graph 100 showing example plots of acoustic speeds through different materials, according to some implementations of the present disclosure. The acoustic speeds include an acoustic speed in hydrocarbon fluid (oil) and hydrocarbon gas and water (saline and pure). Values plotted in the graph 100 are plotted relative to an acoustic velocity axis 102, for example, in meters per second (m/s).

The graph 100 plots different groups of points for different types of information. Salinity points 104 are plotted for a brine concentration (for example, 20,000 ppm) at constant pressure and different temperatures. A pure water point 106 is also plotted. Oil density points 108 are plotted for different APIs for a constant pressure and different temperature combination. Gas density points 110 are plotted for different densities and for different combinations of pressure and temperature. A key 112 identifies different pressure and temperature combinations associated with the points plotted in the graph 100.

FIG. 2 is a graph 200 showing examples of plots of acoustic speeds in a liquid hydrocarbon fluid and water, according to some implementations of the present disclosure. For example, the graph 200 shows acoustic speeds in oil and water (saline and pure). Values plotted in the graph 200 are plotted relative to an acoustic velocity axis 202, for example, in (m/s).

The graph 200 plots different groups of points for different types of information. Salinity points 204 are plotted for a brine concentration (for example, 20,000 ppm) at different pressures and temperatures. A pure water point 206 is also plotted. Oil density points 208 are plotted for different APIs for a different pressure and temperature combination. A key 210 identifies different pressure and temperature combinations associated with the points plotted in the graph 200.

FIG. 3 is a graph 300 showing examples of plots of acoustic speeds in a hydrocarbon gas, according to some implementations of the present disclosure. Values plotted in the graph 300 are plotted relative to an acoustic velocity axis 302, for example, in m/s.

The graph 300 plots different groups of points for different types of information. Gas density points 304 are plotted for different gravities for different pressure and temperature combinations. A key 306 identifies different pressure and temperature combinations associated with the points plotted in the graph 300.

The present disclosure uses techniques that are based on the differences among the acoustic speeds through different materials. For example, fluid type and holdup can be estimated by measuring acoustic velocity passing through different fluids. The present disclosure includes a tool that includes an array of acoustic probes and an opposing array of receivers, as shown in FIGS. 4 and 5.

Figure 4:
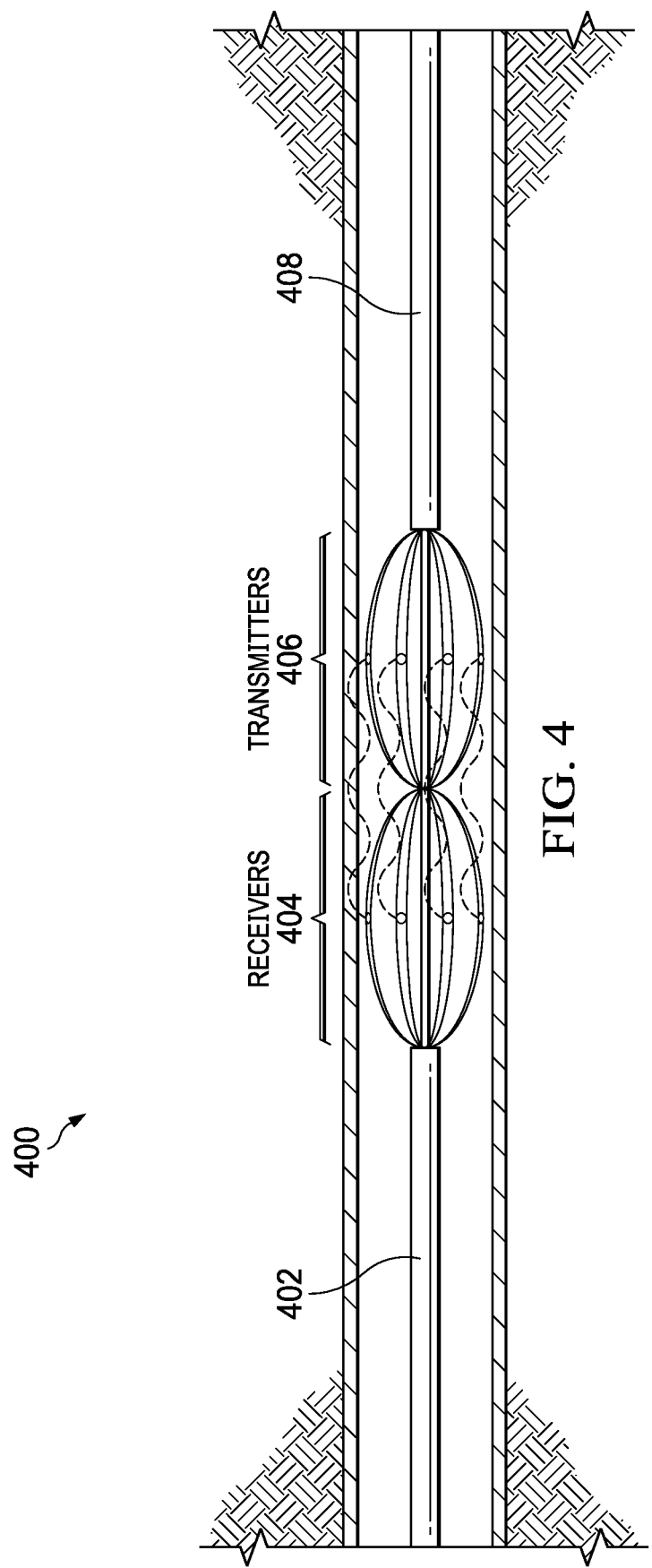
FIG. 4 is a diagram showing an example of an acoustic fluid holdup tool, according to some implementations of the present disclosure.

FIG. 4 is a diagram showing an example of an acoustic fluid holdup tool 400, according to some implementations of the present disclosure. The acoustic fluid holdup tool 400 can be used for horizontal wellbore sections, include array spinners, gyroscope sensor, temperature and pressure sensors. The acoustic fluid holdup tool 400 includes a sound waves processor 402 (or an input processor), sound wave receivers 404 (for example, acoustic wave receivers), sound wave transmitters 406 (for example, acoustic wave transducers, or probes), and a sound wave generator 408 (for example, an acoustic transducers' controller and wave distributor).

FIG. 5A is a diagram 500 showing an example of the use of an acoustic fluid holdup tool in an oil-water two phase, according to some implementations of the present disclosure. The acoustic fluid holdup tool can be used for horizontal wellbore sections, include array spinners, gyroscope sensor, temperature and pressure sensors. For example, the diagram 500 shows the use of the sound wave receivers 404 and the sound wave transmitters 406 in an oil phase 502 and a water phase 504.

The acoustic waves transmitters are connected to an acoustic generator, where each probe transmits waves at a specific frequency that is different from the frequencies of other transmitters. Each opposing receiver is configured to receive only the wave frequency from its opposing transmitter to avoid frequency-based overlapping and interference. An acoustic wave processor can be used to estimate acoustic velocities between each transmitter-receiver pair. The acoustic tool can be used (for example, coupled or integrated) with traditional production logging measurements to estimate bottom hole production rates and fluid holdups. Production logging measurements can include measurements obtained, for example, from spinners, electric resistivity probes, capacitance probes, optical probes, density probes, pressure, and temperature.

Figure 5B:
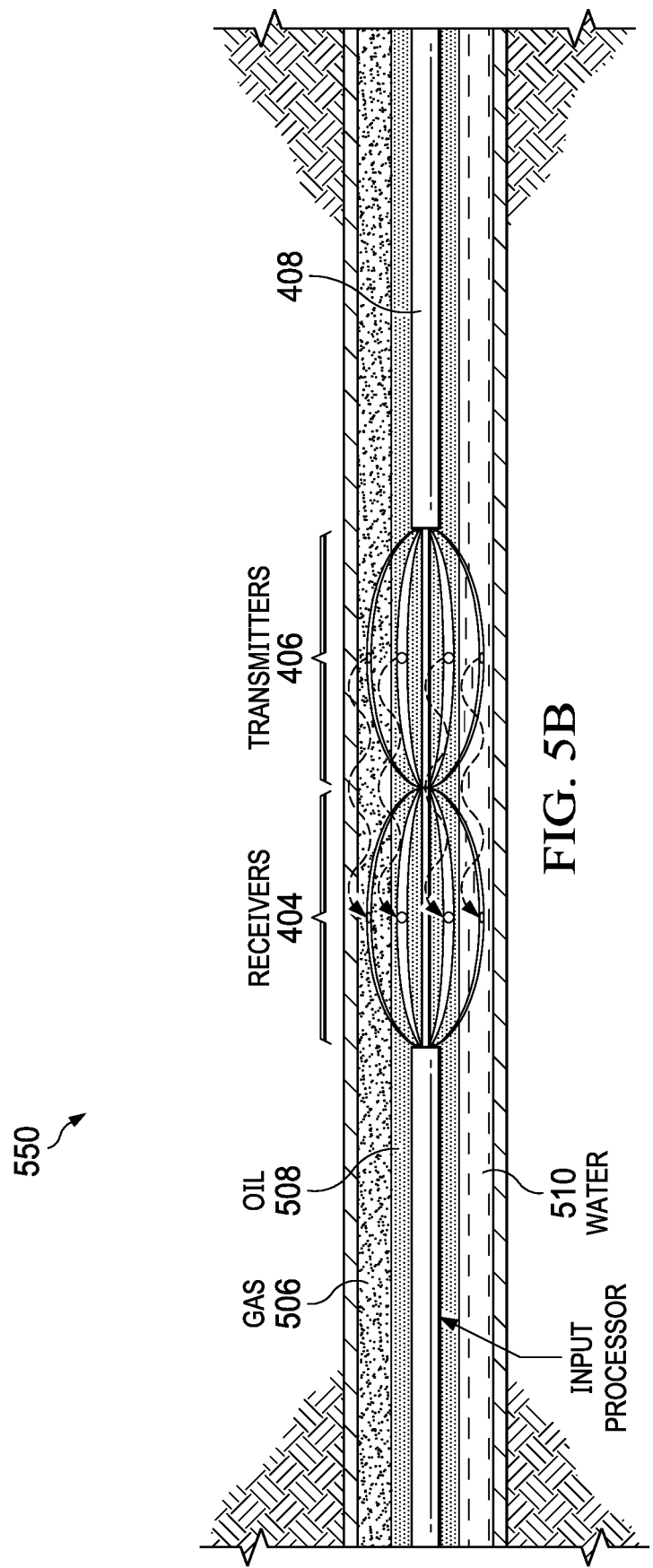
FIG. 5B is a diagram showing an example of the use of an acoustic fluid holdup tool in a gas-oil-water three phase, according to some implementations of the present disclosure.

FIG. 5B is a diagram 550 showing an example of the use of an acoustic fluid holdup tool in a gas-oil-water three phase, according to some implementations of the present disclosure. The acoustic fluid holdup tool can be used for horizontal wellbore sections, include array spinners, gyroscope sensor, temperature and pressure sensors. For example, the diagram 550 shows the use of the sound wave receivers 404 and the sound wave transmitters 406 in a gas phase 506, an oil phase 508, and a water phase 510.

Figure 6:
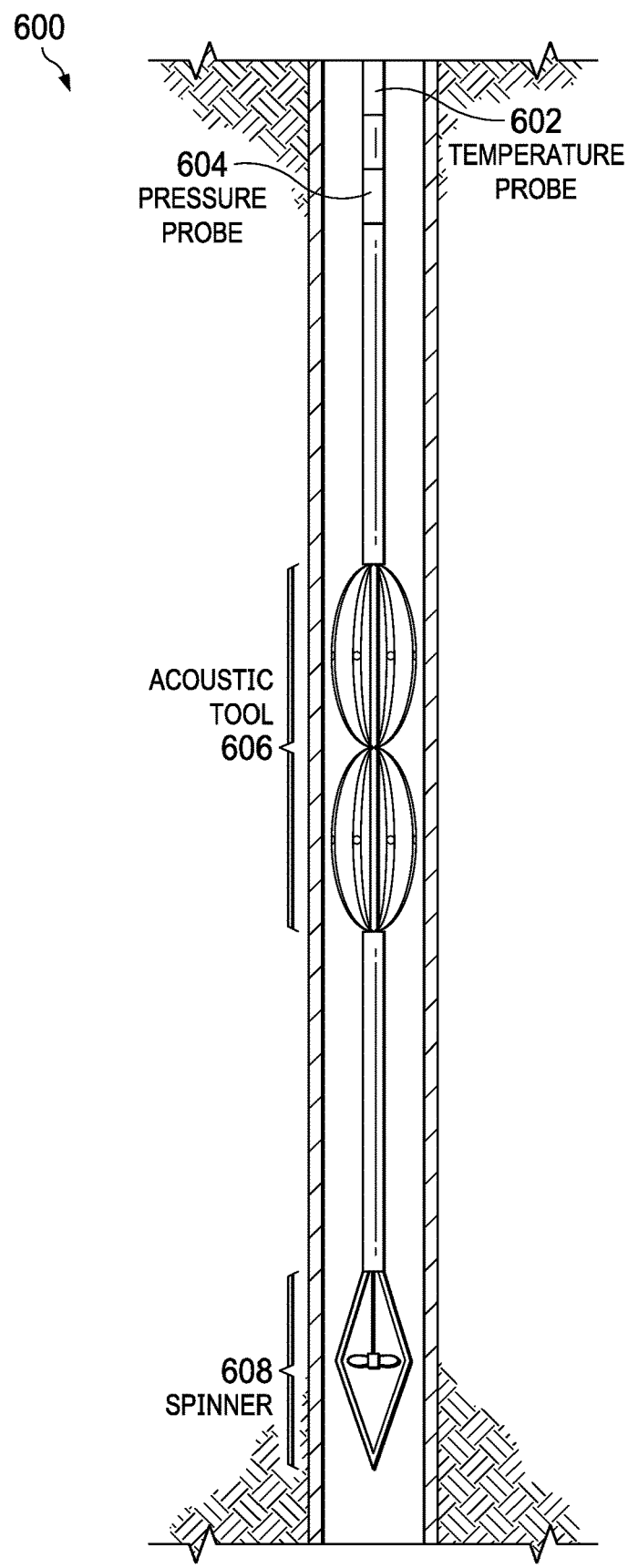
FIG. 6 is a diagram showing an example of an acoustic tool coupled with other measuring probes, according to some implementations of the present disclosure.

FIG. 6 is a diagram 600 showing an example of an acoustic tool coupled with other measuring probes, according to some implementations of the present disclosure. The acoustic tool can be used for vertical/deviated wellbore sections. For example, the measuring probes can include a temperature probe 602, a pressure probe 604, an acoustic tool 606, and a spinner 608. The acoustic tool 606 can include the sound wave receivers 404 and the sound wave transmitters 406, for example.

FIGS. 7A-7D are diagrams showing examples of use of a symmetrical compensated acoustic logging tool at different transmitter/receiver arrangements 702*a*-702*d*, according to some implementations of the present disclosure. The transmitter/receiver arrangements 702*a*-702*d* can apply to different tool directions 704 and different fluids flow directions 706. For example, in a transmitter, receiver, transmitter (TRT) arrangement 702*a*, the tool can be used in a counter-current flow. In a TRT arrangement 702*b*, the tool can be used in a co-current flow. In a receiver, transmitter, receiver (RTR) arrangement 702*c*, the tool can be used in a counter-current flow. In an RTR arrangement 702*d*, the tool can be used in a co-current flow. The symmetrical compensated acoustic logging tool can be used in different applications, including: 1) downhole fluids flow in wellbores (for example, horizontal wellbores, deviated wellbores, and vertical wellbores), and 2) surface pipe flow.

Correlations or predictive charts can be established through lab tests for each fluid type and holdup at different pressures, temperatures, and water salinities to predict fluid holdups, densities, salinities. FIGS. 8 through 12 illustrate some applications for different fluids flow in wellbores or pipes. In some implementations, the graphs shown in FIGS. 8 through 12 can be presented in a graphical user interface.

Figure 8:
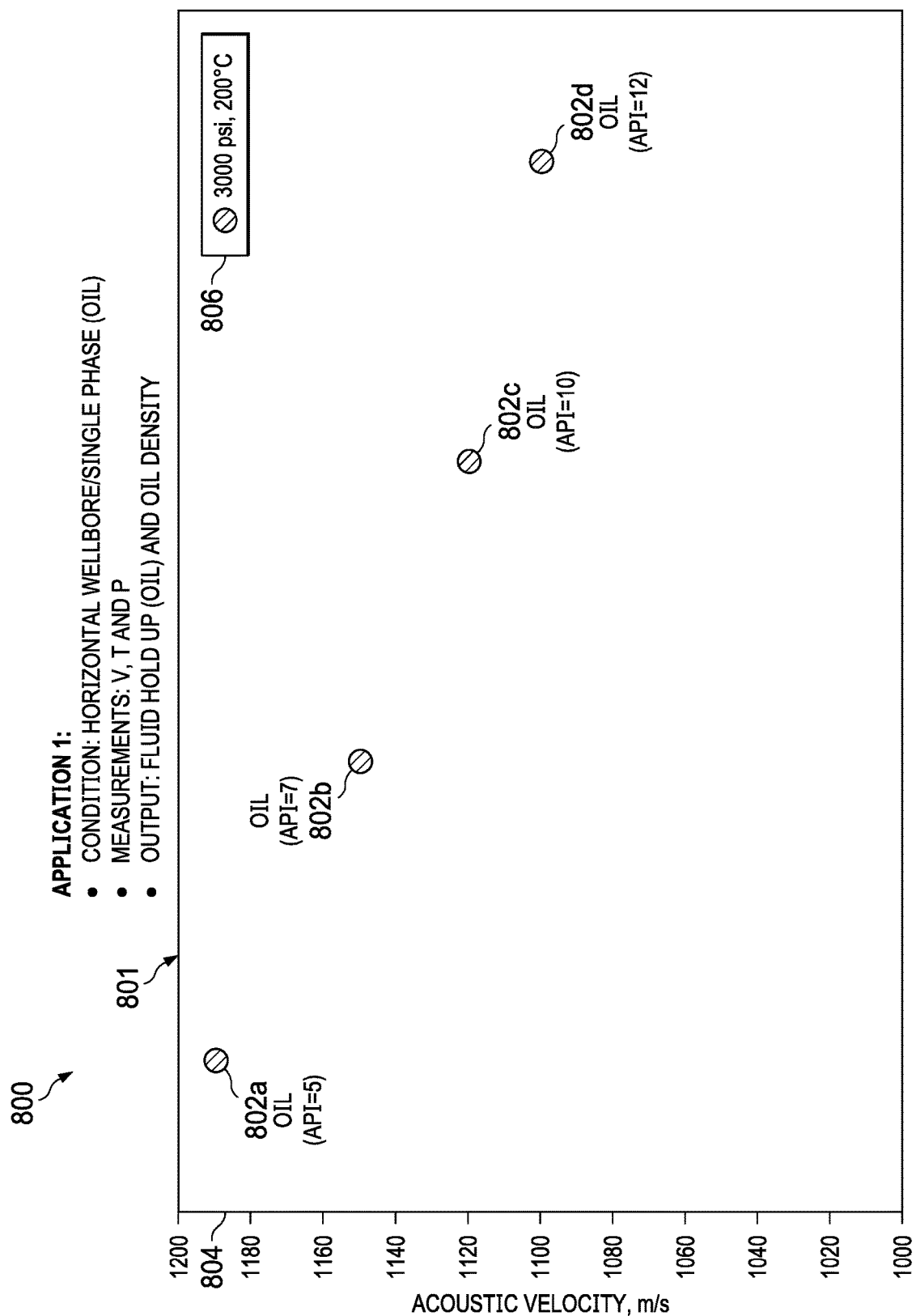
FIGS. 8-12 are graphs showing examples of relationships of values provided by applications, according to some implementations of the present disclosure.

FIG. 8 is a graph 800 showing examples of relationships of values provided by an application 801, according to some implementations of the present disclosure. The application 801 (Application "1") models: the condition of horizontal or vertical/deviated wellbore/single phase (oil); measurements: velocity (V), T, and P; and output of fluid hold up (oil) and oil density. The graph 800 plots oil density points 802*a*-802*d* relative to an acoustic velocity axis 804, for example, in m/s. A key 806 identifies pressure and temperature values associated with the oil density points 802*a*-802*d* (each with different API values).

Figure 9:
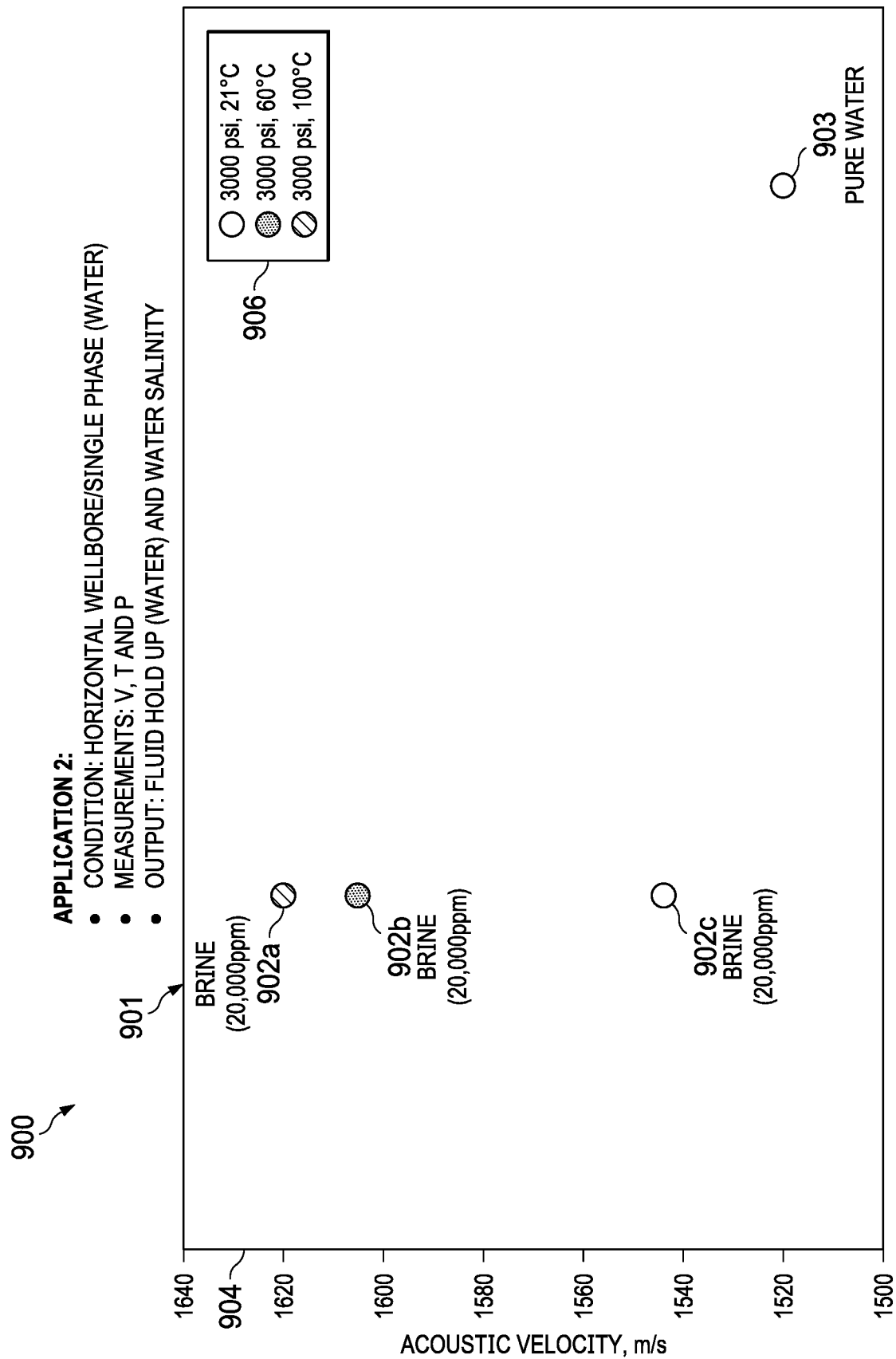

FIG. 9 is a graph 900 showing examples of relationships of values provided by a single phase water application 901, according to some implementations of the present disclosure. The application 901 (Application "2") models: the condition of horizontal or vertical/deviated wellbore/single phase (water); measurements: V, T and P; and output of fluid hold up (water) and water salinity (for example, 20,000 ppm). The graph 900 plots salinity points 902*a*-902*c* and a pure water point 903 relative to an acoustic velocity axis 904, for example, in m/s. A key 906 identifies different pressure and temperature combinations associated with the salinity points 902*a*-902*c*, each being for a brine concentration of 20,000 ppm, but at different acoustic velocities.

Figure 10:
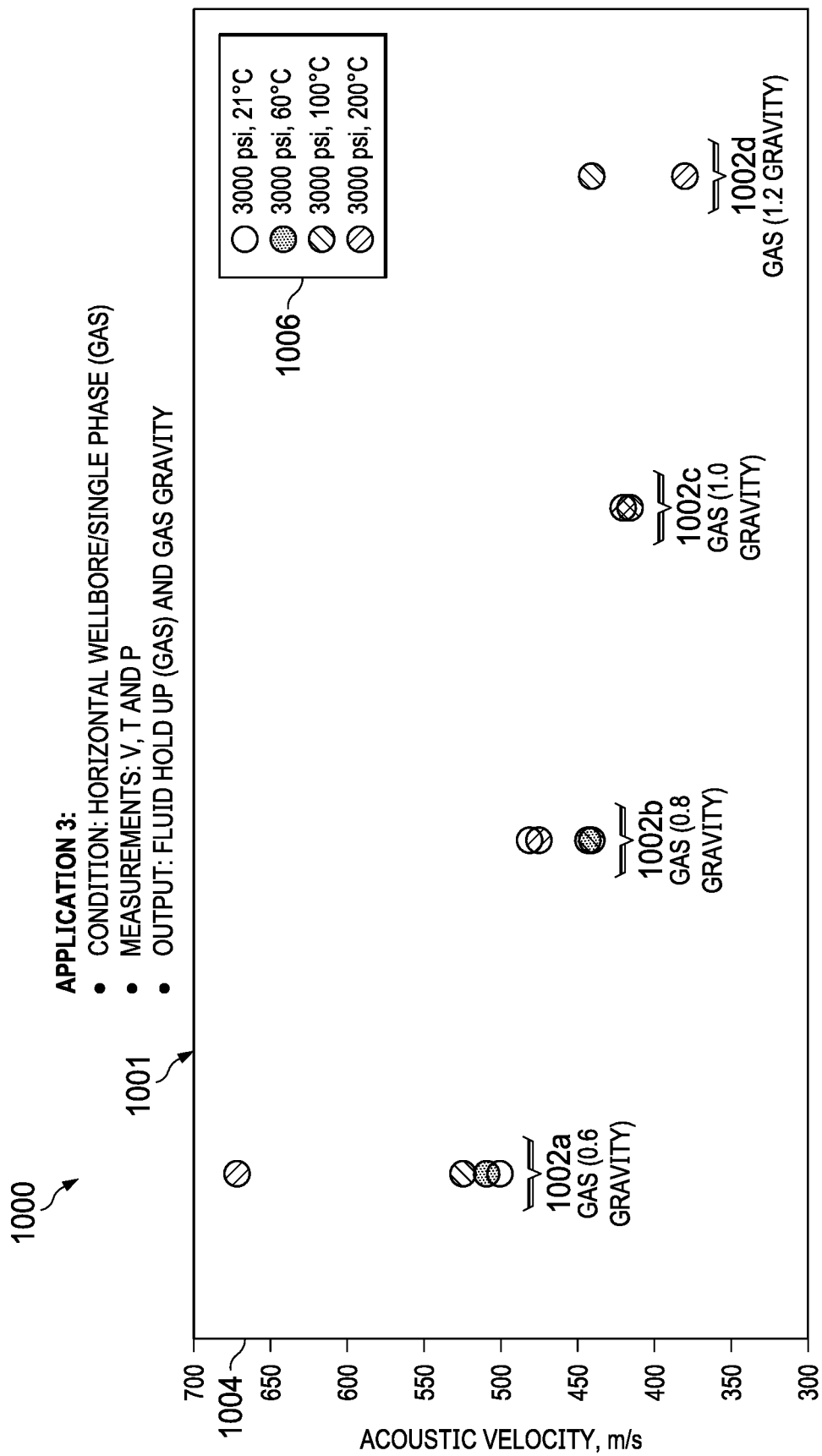

FIG. 10 is a graph 1000 showing examples of relationships of values provided by a single phase gas application 1001, according to some implementations of the present disclosure. The application 1001 (Application "3") models: the condition of horizontal or vertical/deviated wellbore/single phase (gas); measurements: V, T, and P; and output: fluid hold up (gas) and gas gravity. The graph 1000 plots gravity points 1002*a*-1002*d* relative to an acoustic velocity axis 1004, for example, in m/s. A key 1006 identifies pressure and temperature values associated with the gas gravity points 1002*a*-1002*d* (each with different gravity values).

Figure 11:
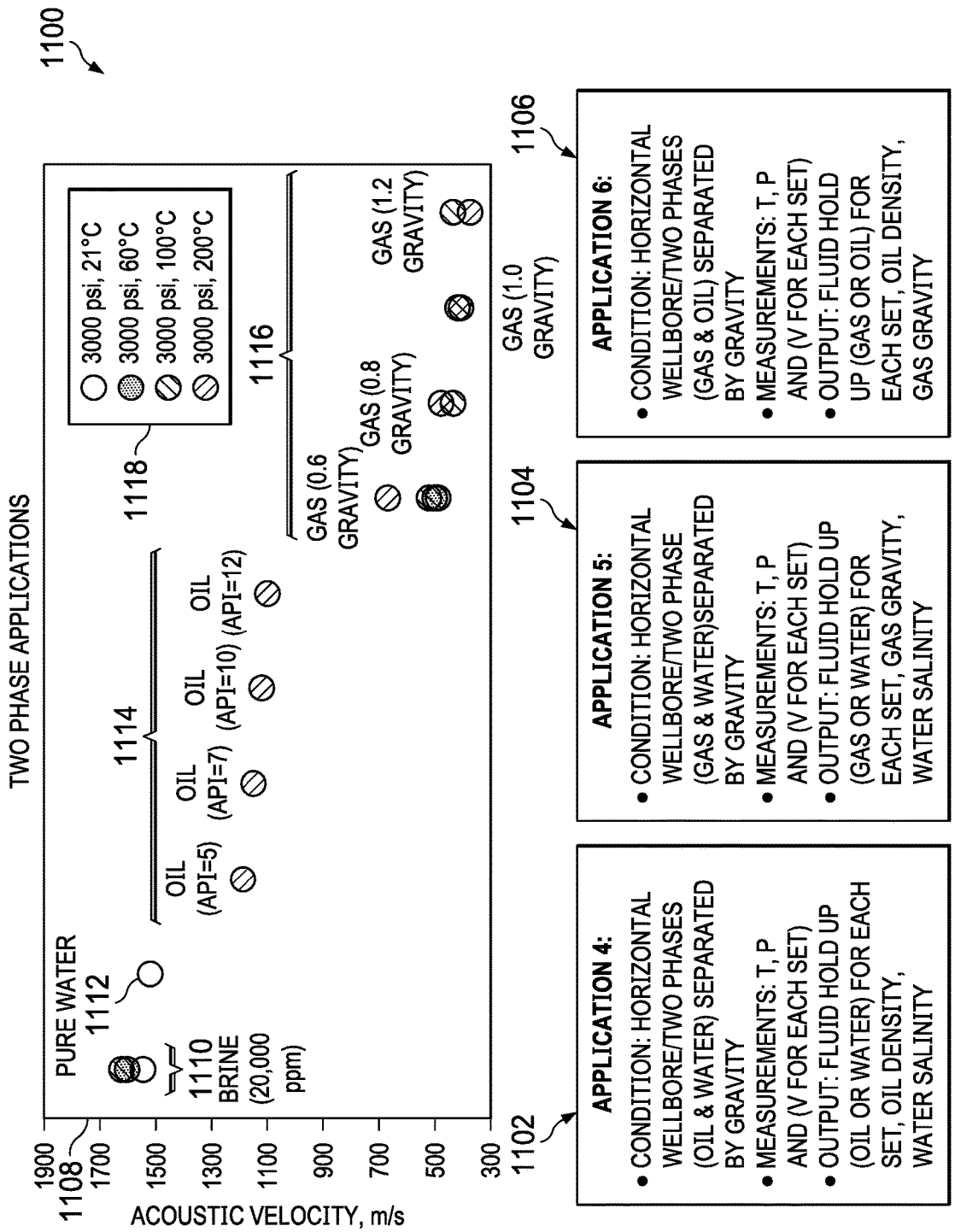

FIG. 11 is a graph 1100 showing examples of relationships of values provided by two phase applications 1102, 1104, and 1106, according to some implementations of the present disclosure. Values plotted in the graph are plotted relative to an acoustic velocity axis 1108, for example, in m/s.

The application 1102 (Application "4") models: the condition of horizontal wellbore/two phases (oil and water) separated or segregated by gravity; measurements: T, P, and (V for each set, referring to a pair of transmitter (transducer) and receiver); and output: fluid holdup (oil or water) for each set, oil density, water salinity. Emulsion can be predicted if the measured acoustic speed Vm is between oil acoustic speed Voil and water acoustic speed Vwater. Therefore, if Vm is close to Vwater then it's "oil in water" emulsion. If Vm is close to Voil then it's "water in oil" emulsion. In case of vertical/deviated wellbore (mixture oil and water), Voil and Vwater are measured during shut-in for each phase then Vm of flowing mixture is measured during flowing passes. Correlations and predictive charts can be used to extrapolate fluid holdups and properties of each phase during flowing (mixed fluids)

The application 1104 (Application "5") models: the condition of horizontal wellbore/two phase (gas and water) separated by gravity; measurements: T, P, and (V for each set); and output: fluid holdup (gas or water) for each set, gas gravity, water salinity. In case of vertical/deviated wellbore (mixture gas and water), Vwater is measured during shut-in Vgas can be assumed from PVT and gas acoustic speed charts at different pressure and temperature. Then, Vm of flowing mixture is measured during flowing passes. Correlations and predictive charts can be used to extrapolate fluid holdups and properties of each phase during flowing (mixed fluids)

The application 1106 (Application "6") models: the condition of horizontal wellbore/two phases (gas and oil) separated by gravity; measurements: T, P and (V for each set); and output: fluid holdup (gas or oil) for each set, oil density, gas gravity. In case of vertical/deviated wellbore (mixture gas and oil), Voil is measured during shut-in where Vgas can be assumed from PVT and gas acoustic speed charts at different pressure and temperature. Then, Vm of flowing mixture is measured during flowing passes. Correlations and predictive charts can be used to extrapolate fluid holdups and properties of each phase during flowing (mixed fluids)

The graph 1100 plots different groups of points for different types of information. Salinity points 1110 are plotted for a brine concentration (for example, 20,000 ppm) at different pressures and temperatures. A pure water point 1112 is also plotted. Oil density points 1114 are plotted for different APIs for a constant pressure and temperature combination. Gas density points 1116 are plotted for different densities and for different combinations of pressure and temperature. A key 1118 identifies different pressure and temperature combinations associated with the points plotted in the graph 1100.

Figure 12:
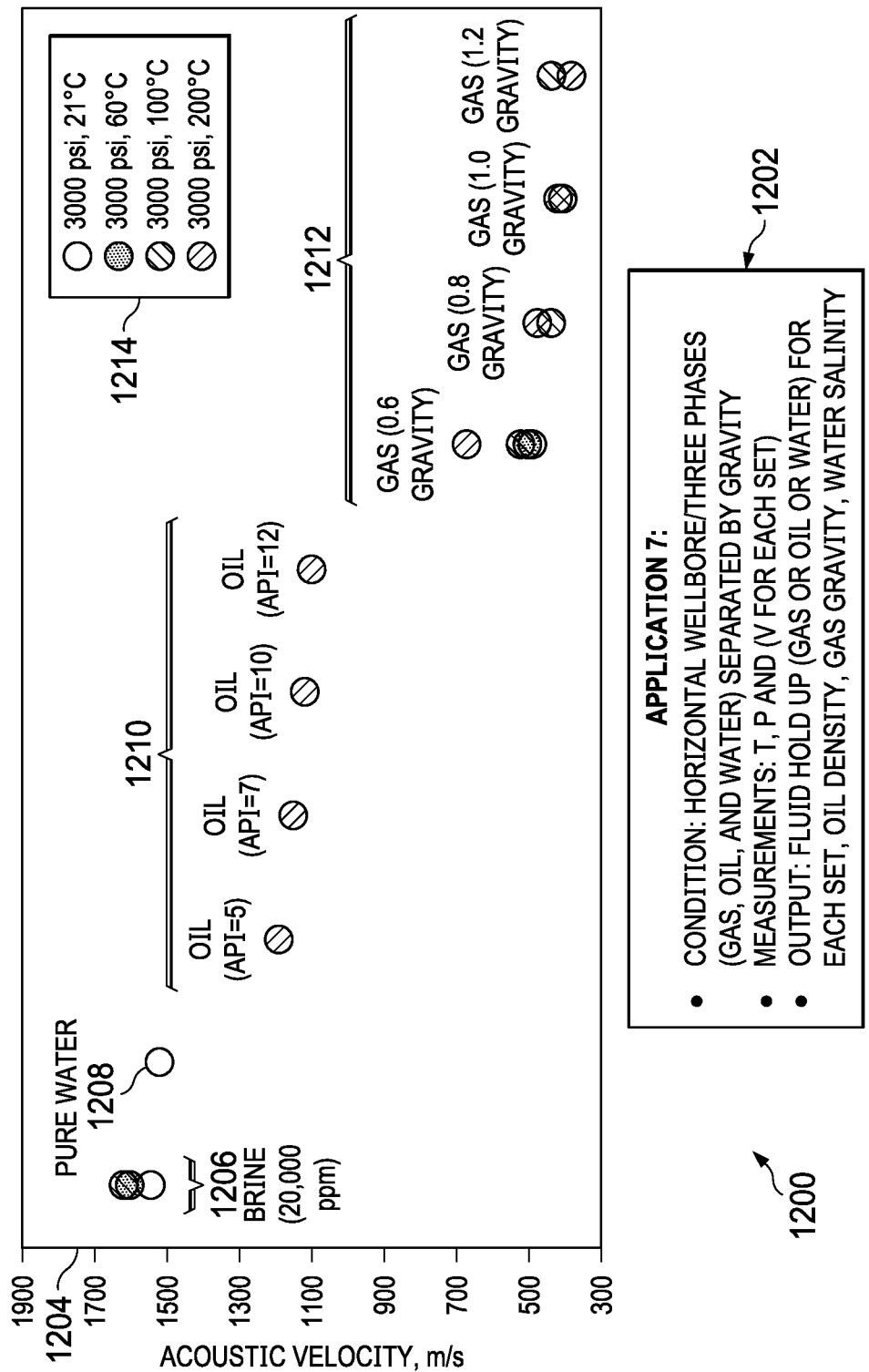

FIG. 12 is a graph 1200 showing examples of relationships of values provided by a three-phase application 1202, according to some implementations of the present disclosure. Values plotted in the graph 1200 are plotted relative to an acoustic velocity axis 1204, for example, in m/s.

The application 1202 (Application "7") models: the condition of horizontal wellbore/three phases (gas, oil, and water) separated by gravity; measurements: T, P and (V for each set); and output: fluid holdup (gas or oil or water) for each set, oil density, gas gravity, water salinity. In case of vertical/deviated wellbore (mixture gas, oil and water), Voil and Vwater are measured during shut-in where Vgas can be assumed from PVT and gas acoustic speed charts at different pressure and temperature. Then, Vm of flowing mixture is measured during flowing passes. Correlations and predictive charts can be used to extrapolate fluid holdups and properties of each phase during flowing (mixed fluids)

The graph 1200 plots different groups of points for different types of information. Salinity points 1206 are plotted for a brine concentration (for example, 20,000 ppm) at different pressures and temperatures. A pure water point 1208 is also plotted. Oil density points 1210 are plotted for different APIs for a constant pressure and different temperature combination. Gas density points 1212 are plotted for different densities and for different combinations of pressure and temperature. A key 1214 identifies different pressure and temperature combinations associated with the points plotted in the graph 1200.

Figure 13:
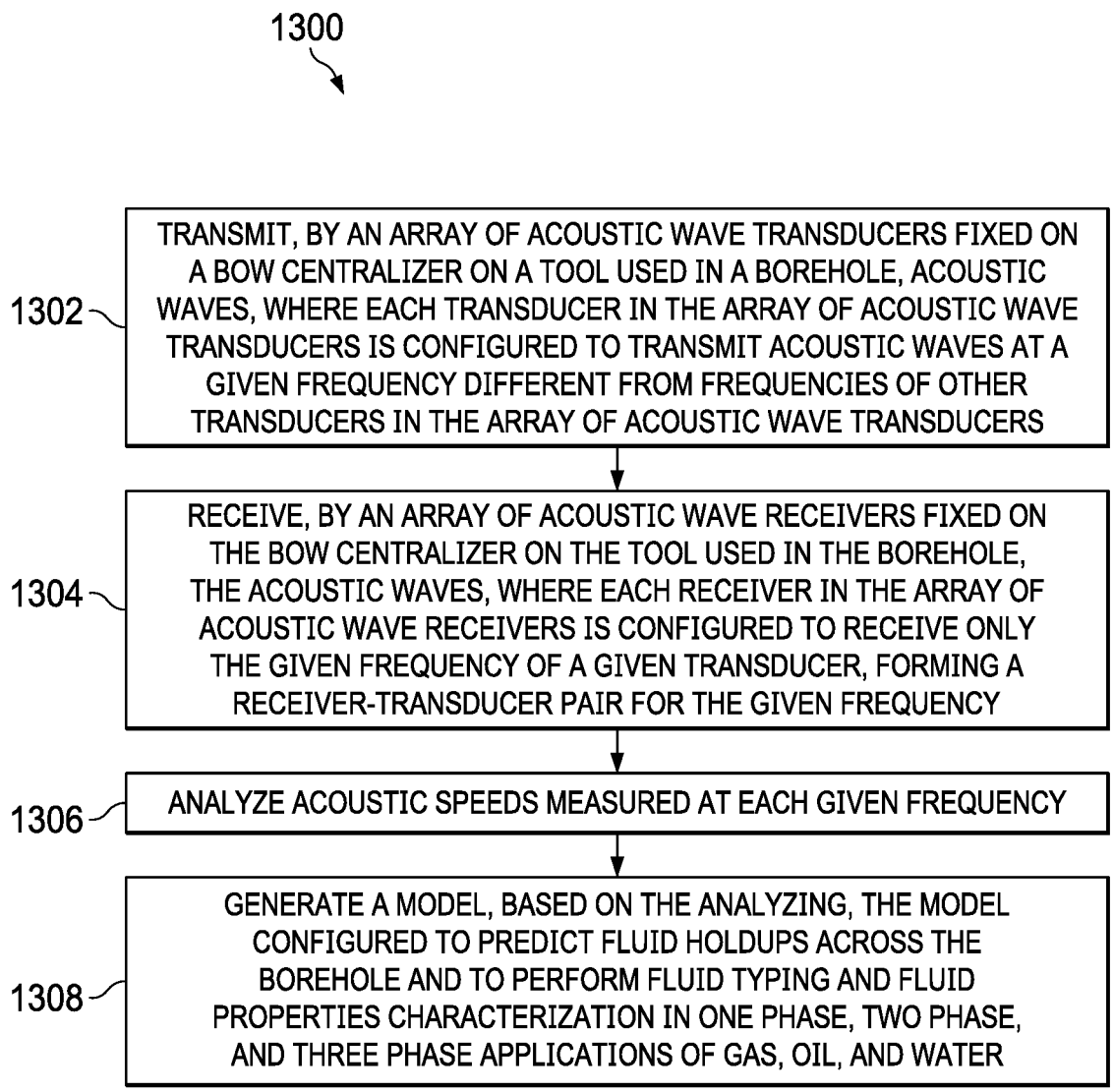
FIG. 13 is a flowchart of an example of a method for using acoustic waves obtained using arrays of transmitters and receivers to perform fluid typing and fluid properties characterization in one-, two-, and three-phase applications of gas, oil, and water, according to some implementations of the present disclosure.

FIG. 13 is a flowchart of an example of a method 1300 for using acoustic waves obtained using arrays of transmitters and receivers to perform fluid typing and fluid properties characterization in one-, two-, and three-phase applications of gas, oil, and water, according to some implementations of the present disclosure. For clarity of presentation, the description that follows generally describes method 1300 in the context of the other figures in this description. However, it will be understood that method 1300 can be performed, for example, by any suitable system, environment, software, and hardware, or a combination of systems, environments, software, and hardware, as appropriate. In some implementations, various steps of method 1300 can be run in parallel, in combination, in loops, or in any order.

At 1302, acoustic waves are transmitted by an array of acoustic wave transducers fixed on a bow centralizer on a tool used in a borehole or pipe on surface. Each transducer in the array of acoustic wave transducers is configured to transmit acoustic waves at a given frequency different from frequencies of other transducers in the array of acoustic wave transducers. As an example, sound waves can be transmitted by the sound wave transmitters 406. From 1302, method 1300 proceeds to 1304.

At 1304, the acoustic waves are received by an array of acoustic wave receivers fixed on the bow centralizer on the tool used in the borehole or pipe on surface. Each receiver in the array of acoustic wave receivers is configured to receive only the given frequency of a given transducer, forming a receiver-transducer pair for the given frequency. As an example, the sound waves can be received by the sound wave receivers 404. From 1304, method 1300 proceeds to 1306.

At 1306, acoustic speeds measured at each given frequency are analyzed. As an example, the sound waves processor 402 can process the sound waves received by the sound wave receivers 404. From 1306, method 1300 proceeds to 1308.

At 1308, a model is generated based on the analyzing. The model is configured to predict fluid holdups along the borehole and to perform fluid typing and fluid properties characterization in one phase, two phase, and three phase applications of gas, oil, and water. For example, data values predicted by applications can be predicted, as described with reference to FIGS. 8-12. After 1308, method 1300 can stop.

Figure 14:
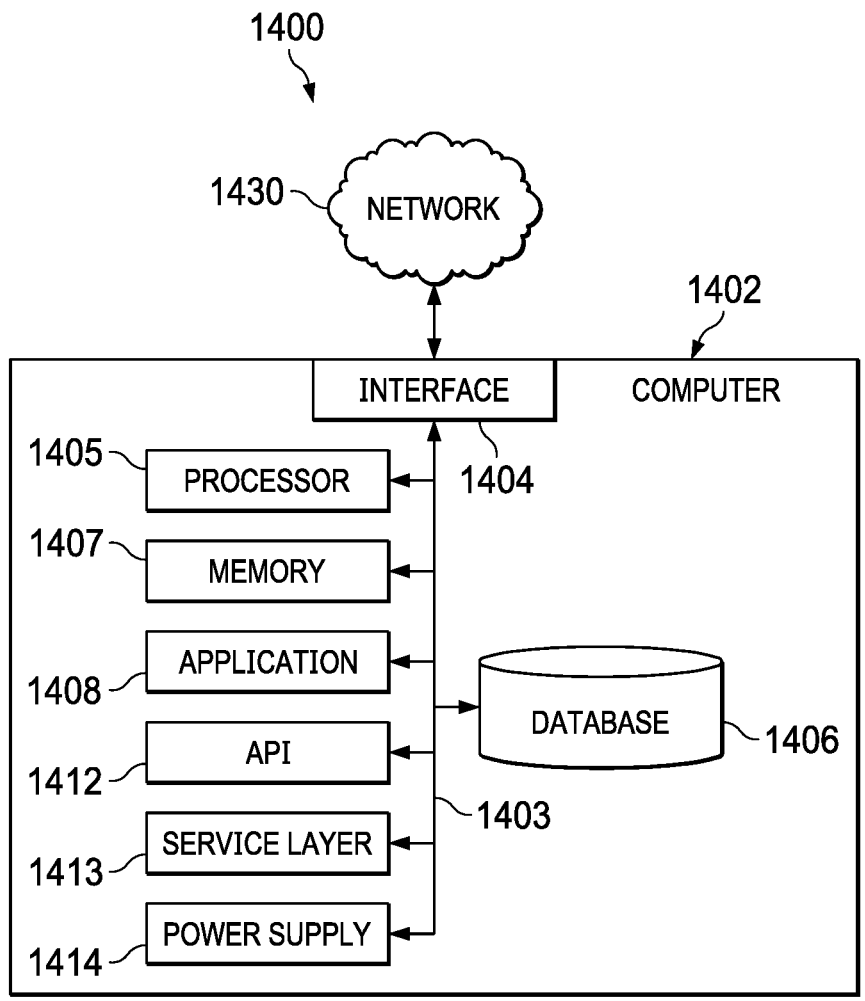
FIG. 14 is a block diagram illustrating an example computer system used to provide computational functionalities associated with described algorithms, methods, functions, processes, flows, and procedures as described in the present disclosure, according to some implementations of the present disclosure.

FIG. 14 is a block diagram of an example computer system 1400 used to provide computational functionalities associated with described algorithms, methods, functions, processes, flows, and procedures described in the present disclosure, according to some implementations of the present disclosure. The illustrated computer 1402 is intended to encompass any computing device such as a server, a desktop computer, a laptop/notebook computer, a wireless data port, a smart phone, a personal data assistant (PDA), a tablet computing device, or one or more processors within these devices, including physical instances, virtual instances, or both. The computer 1402 can include input devices such as keypads, keyboards, and touch screens that can accept user information. Also, the computer 1402 can include output devices that can convey information associated with the operation of the computer 1402. The information can include digital data, visual data, audio information, or a combination of information. The information can be presented in a graphical user interface (UI) (or GUI).

The computer 1402 can serve in a role as a client, a network component, a server, a database, a persistency, or components of a computer system for performing the subject matter described in the present disclosure. The illustrated computer 1402 is communicably coupled with a network 1430. In some implementations, one or more components of the computer 1402 can be configured to operate within different environments, including cloud-computing-based environments, local environments, global environments, and combinations of environments.

At a top level, the computer 1402 is an electronic computing device operable to receive, transmit, process, store, and manage data and information associated with the described subject matter. According to some implementations, the computer 1402 can also include, or be communicably coupled with, an application server, an email server, a web server, a caching server, a streaming data server, or a combination of servers.

The computer 1402 can receive requests over network 1430 from a client application (for example, executing on another computer 1402). The computer 1402 can respond to the received requests by processing the received requests using software applications. Requests can also be sent to the computer 1402 from internal users (for example, from a command console), external (or third) parties, automated applications, entities, individuals, systems, and computers.

Each of the components of the computer 1402 can communicate using a system bus 1403. In some implementations, any or all of the components of the computer 1402, including hardware or software components, can interface with each other or the interface 1404 (or a combination of both) over the system bus 1403. Interfaces can use an application programming interface (API) 1412, a service layer 1413, or a combination of the API 1412 and service layer 1413. The API 1412 can include specifications for routines, data structures, and object classes. The API 1412 can be either computer-language independent or dependent. The API 1412 can refer to a complete interface, a single function, or a set of APIs.

The service layer 1413 can provide software services to the computer 1402 and other components (whether illustrated or not) that are communicably coupled to the computer 1402. The functionality of the computer 1402 can be accessible for all service consumers using this service layer. Software services, such as those provided by the service layer 1413, can provide reusable, defined functionalities through a defined interface. For example, the interface can be software written in JAVA, C++, or a language providing data in extensible markup language (XML) format. While illustrated as an integrated component of the computer 1402, in alternative implementations, the API 1412 or the service layer 1413 can be stand-alone components in relation to other components of the computer 1402 and other components communicably coupled to the computer 1402. Moreover, any or all parts of the API 1412 or the service layer 1413 can be implemented as child or sub-modules of another software module, enterprise application, or hardware module without departing from the scope of the present disclosure.

The computer 1402 includes an interface 1404. Although illustrated as a single interface 1404 in FIG. 14, two or more interfaces 1404 can be used according to particular needs, desires, or particular implementations of the computer 1402 and the described functionality. The interface 1404 can be used by the computer 1402 for communicating with other systems that are connected to the network 1430 (whether illustrated or not) in a distributed environment. Generally, the interface 1404 can include, or be implemented using, logic encoded in software or hardware (or a combination of software and hardware) operable to communicate with the network 1430. More specifically, the interface 1404 can include software supporting one or more communication protocols associated with communications. As such, the network 1430 or the interface's hardware can be operable to communicate physical signals within and outside of the illustrated computer 1402.

The computer 1402 includes a processor 1405. Although illustrated as a single processor 1405 in FIG. 14, two or more processors 1405 can be used according to particular needs, desires, or particular implementations of the computer 1402 and the described functionality. Generally, the processor 1405 can execute instructions and can manipulate data to perform the operations of the computer 1402, including operations using algorithms, methods, functions, processes, flows, and procedures as described in the present disclosure.

The computer 1402 also includes a database 1406 that can hold data for the computer 1402 and other components connected to the network 1430 (whether illustrated or not). For example, database 1406 can be an in-memory, conventional, or a database storing data consistent with the present disclosure. In some implementations, database 1406 can be a combination of two or more different database types (for example, hybrid in-memory and conventional databases) according to particular needs, desires, or particular implementations of the computer 1402 and the described functionality. Although illustrated as a single database 1406 in FIG. 14, two or more databases (of the same, different, or combination of types) can be used according to particular needs, desires, or particular implementations of the computer 1402 and the described functionality. While database 1406 is illustrated as an internal component of the computer 1402, in alternative implementations, database 1406 can be external to the computer 1402.

The computer 1402 also includes a memory 1407 that can hold data for the computer 1402 or a combination of components connected to the network 1430 (whether illustrated or not). Memory 1407 can store any data consistent with the present disclosure. In some implementations, memory 1407 can be a combination of two or more different types of memory (for example, a combination of semiconductor and magnetic storage) according to particular needs, desires, or particular implementations of the computer 1402 and the described functionality. Although illustrated as a single memory 1407 in FIG. 14, two or more memories 1407 (of the same, different, or combination of types) can be used according to particular needs, desires, or particular implementations of the computer 1402 and the described functionality. While memory 1407 is illustrated as an internal component of the computer 1402, in alternative implementations, memory 1407 can be external to the computer 1402.

The application 1408 can be an algorithmic software engine providing functionality according to particular needs, desires, or particular implementations of the computer 1402 and the described functionality. For example, application 1408 can serve as one or more components, modules, or applications. Further, although illustrated as a single application 1408, the application 1408 can be implemented as multiple applications 1408 on the computer 1402. In addition, although illustrated as internal to the computer 1402, in alternative implementations, the application 1408 can be external to the computer 1402.

The computer 1402 can also include a power supply 1414. The power supply 1414 can include a rechargeable or non-rechargeable battery that can be configured to be either user- or non-user-replaceable. In some implementations, the power supply 1414 can include power-conversion and management circuits, including recharging, standby, and power management functionalities. In some implementations, the power-supply 1414 can include a power plug to allow the computer 1402 to be plugged into a wall socket or a power source to, for example, power the computer 1402 or recharge a rechargeable battery.

There can be any number of computers 1402 associated with, or external to, a computer system containing computer 1402, with each computer 1402 communicating over network 1430. Further, the terms "client," "user," and other appropriate terminology can be used interchangeably, as appropriate, without departing from the scope of the present disclosure. Moreover, the present disclosure contemplates that many users can use one computer 1402 and one user can use multiple computers 1402.

Described implementations of the subject matter can include one or more features, alone or in combination.

For example, in a first implementation, a computer-implemented method includes the following. Acoustic waves are transmitted by an array of acoustic wave transducers fixed on a bow centralizer on a tool used in a borehole or pipe on surface. Each transducer in the array of acoustic wave transducers is configured to transmit acoustic waves at a given frequency different from frequencies of other transducers in the array of acoustic wave transducers. The acoustic waves are received by an array of acoustic wave receivers fixed on the bow centralizer on the tool used in the borehole. Each receiver in the array of acoustic wave receivers is configured to receive only the given frequency of a given transducer, forming a receiver-transducer pair for the given frequency. Acoustic speeds measured at each given frequency are analyzed. A model is generated based on the analyzing. The model is configured to predict fluid holdups across the borehole and to perform fluid typing and fluid properties characterization in one phase, two phase, and three phase applications of gas, oil, and water.

The foregoing and other described implementations can each, optionally, include one or more of the following features:

A first feature, combinable with any of the following features, where analyzing the acoustic speeds and generating the model includes: using information from array production logs obtained using an array of spinners, the information used to determine flow rates of each fluid type; using the model to estimate fluid type, density, and water salinity for each fluid type with known acoustic speed of fluids at specific pressure and temperature; and generating correlations and predictive charts using lab tests for each fluid type and holdup at different pressures, temperatures, and water salinities, where the correlations and predictive charts are configured to predict fluid holdups, densities, and salinities.

A second feature, combinable with any of the previous or following features, where the model includes one phase applications, including: a single phase oil application modeling the condition of a single phase oil, using velocity (V), pressure (P), and temperature (T) measurements, and creating an output of oil density; a single phase water application modeling the condition of a single phase water, using V, P, and T measurements, and creating an output of salinity; and a single phase gas application modeling the condition of a single phase gas, using V, P, and T measurements, and creating an output of gas gravity.

A third feature, combinable with any of the previous or following features, where the model includes two phase applications, including: a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity; a double phase application modeling the condition of a horizontal wellbore with two phases including gas and water segregated by gravity; measurements T, P, and V for each set; and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

A fourth feature, combinable with any of the previous or following features, where the model includes a three phase application, including: a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

A fifth feature, combinable with any of the previous or following features, the method further including: using the array of acoustic wave transducers and the array of acoustic wave receivers in a symmetrical compensated acoustic logging tool; and executing the symmetrical compensated acoustic logging tool at different transmitter/receiver arrangements and in different fluid flow directions.

A sixth feature, combinable with any of the previous or following features, the method further including: plotting, in a graphical user interface, values determined using the model, where the values include salinity values, oil density values, and gas density values at different combinations of V, P, and T, where the values are plotted relative to an acoustic velocity axis, and where the values are annotated to indicate specific combinations of P and T.

In a second implementation, a non-transitory, computer-readable medium stores one or more instructions executable by a computer system to perform operations including the following. Acoustic waves are transmitted by an array of acoustic wave transducers fixed on a bow centralizer on a tool used in a borehole. Each transducer in the array of acoustic wave transducers is configured to transmit acoustic waves at a given frequency different from frequencies of other transducers in the array of acoustic wave transducers. The acoustic waves are received by an array of acoustic wave receivers fixed on the bow centralizer on the tool used in the borehole. Each receiver in the array of acoustic wave receivers is configured to receive only the given frequency of a given transducer, forming a receiver-transducer pair for the given frequency. Acoustic speeds measured at each given frequency are analyzed. A model is generated based on the analyzing. The model is configured to predict fluid holdups across the borehole and to perform fluid typing and fluid properties characterization in one phase, two phase, and three phase applications of gas, oil, and water.

The foregoing and other described implementations can each, optionally, include one or more of the following features:

A first feature, combinable with any of the following features, where analyzing the acoustic speeds and generating the model includes: using information from array production logs obtained using an array of spinners, the information used to determine flow rates of each fluid type; using the model to estimate fluid type, density, and water salinity for each fluid type with known acoustic speed of fluids at specific pressure and temperature; and generating correlations and predictive charts using lab tests for each fluid type and holdup at different pressures and temperatures, where the correlations and predictive charts are configured to predict fluid holdups, densities, and salinities.

A second feature, combinable with any of the previous or following features, where the model includes one phase applications, including: a single phase oil application modeling the condition of a single phase oil, using velocity (V), pressure (P), and temperature (T) measurements, and creating an output of oil density; a single phase water application modeling the condition of a single phase water, using V, P, and T measurements, and creating an output of salinity; and a single phase gas application modeling the condition of a single phase gas, using V, P, and T measurements, and creating an output of gas gravity.

A third feature, combinable with any of the previous or following features, where the model includes two phase applications, including: a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity; a double phase application modeling the condition of a horizontal wellbore with two phases including gas and water segregated by gravity; measurements T, P, and V for each set; and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

A fourth feature, combinable with any of the previous or following features, where the model includes a three phase application, including: a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

A fifth feature, combinable with any of the previous or following features, the operations further including: using the array of acoustic wave transducers and the array of acoustic wave receivers in a symmetrical compensated acoustic logging tool; and executing the symmetrical compensated acoustic logging tool at different transmitter/receiver arrangements and in different fluid flow directions.

A sixth feature, combinable with any of the previous or following features, the operations further including: plotting, in a graphical user interface, values determined using the model, where the values include salinity values, oil density values, and gas density values at different combinations of V, P, and T, where the values are plotted relative to an acoustic velocity axis, and where the values are annotated to indicate specific combinations of P and T.

In a third implementation, a computer-implemented system includes one or more processors and a non-transitory computer-readable storage medium coupled to the one or more processors and storing programming instructions for execution by the one or more processors. The programming instructions instruct the one or more processors to perform operations including the following. Acoustic waves are transmitted by an array of acoustic wave transducers fixed on a bow centralizer on a tool used in a borehole. Each transducer in the array of acoustic wave transducers is configured to transmit acoustic waves at a given frequency different from frequencies of other transducers in the array of acoustic wave transducers. The acoustic waves are received by an array of acoustic wave receivers fixed on the bow centralizer on the tool used in the borehole. Each receiver in the array of acoustic wave receivers is configured to receive only the given frequency of a given transducer, forming a receiver-transducer pair for the given frequency. Acoustic speeds measured at each given frequency are analyzed. A model is generated based on the analyzing. The model is configured to predict fluid holdups across the borehole and to perform fluid typing and fluid properties characterization in one phase, two phase, and three phase applications of gas, oil, and water.

The foregoing and other described implementations can each, optionally, include one or more of the following features:

A first feature, combinable with any of the following features, where analyzing the acoustic speeds and generating the model includes: using information from array production logs obtained using an array of spinners, the information used to determine flow rates of each fluid type; using the model to estimate fluid type, density, and water salinity for each fluid type with known acoustic speed of fluids at specific pressure and temperature; and generating correlations and predictive charts using lab tests for each fluid type and holdup at different pressures, temperatures, and water salinities, where the correlations and predictive charts are configured to predict fluid holdups, densities, and salinities.

A second feature, combinable with any of the previous or following features, where the model includes one phase applications, including: a single phase oil application modeling the condition of a single phase oil, using velocity (V), pressure (P), and temperature (T) measurements, and creating an output of oil density; a single phase water application modeling the condition of a single phase water, using V, P, and T measurements, and creating an output of salinity; and a single phase gas application modeling the condition of a single phase gas, using V, P, and T measurements, and creating an output of gas gravity.

A third feature, combinable with any of the previous or following features, where the model includes two phase applications, including: a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity; a double phase application modeling the condition of a horizontal wellbore with two phases including gas and water segregated by gravity; measurements T, P, and V for each set; and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

A fourth feature, combinable with any of the previous or following features, where the model includes a three phase application, including: a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

A fifth feature, combinable with any of the previous or following features, the operations further including: using the array of acoustic wave transducers and the array of acoustic wave receivers in a symmetrical compensated acoustic logging tool; and executing the symmetrical compensated acoustic logging tool at different transmitter/receiver arrangements and in different fluid flow directions.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially generated propagated signal. For example, the signal can be a machine-generated electrical, optical, or electromagnetic signal that is generated to encode information for transmission to a suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatuses, devices, and machines for processing data, including by way of example, a programmable processor, a computer, or multiple processors or computers. The apparatus can also include special purpose logic circuitry including, for example, a central processing unit (CPU), a field-programmable gate array (FPGA), or an application-specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, such as LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub-programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory.

Graphics processing units (GPUs) can also be used in combination with CPUs. The GPUs can provide specialized processing that occurs in parallel to processing performed by CPUs. The specialized processing can include artificial intelligence (AI) applications and processing, for example. GPUs can be used in GPU clusters or in multi-GPU computing.

A computer can include, or be operatively coupled to, one or more mass storage devices for storing data. In some implementations, a computer can receive data from, and transfer data to, the mass storage devices including, for example, magnetic, magneto-optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer-readable media (transitory or non-transitory, as appropriate) suitable for storing computer program instructions and data can include all forms of permanent/non-permanent and volatile/non-volatile memory, media, and memory devices. Computer-readable media can include, for example, semiconductor memory devices such as random access memory (RAM), read-only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer-readable media can also include, for example, magnetic devices such as tape, cartridges, cassettes, and internal/removable disks. Computer-readable media can also include magneto-optical disks and optical memory devices and technologies including, for example, digital video disc (DVD), CD-ROM, DVD+/−R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated into, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback including, for example, sensory feedback including visual feedback, auditory feedback, or tactile feedback. Input from the user can be received in the form of acoustic, speech, or tactile input. In addition, a computer can interact with a user by sending documents to, and receiving documents from, a device that the user uses. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch-screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back-end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations. It should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system including a computer memory interoperably coupled with a hardware processor configured to perform the computer-implemented method or the instructions stored on the non-transitory, computer-readable medium.

What is claimed is:

1. A computer-implemented method, comprising:
transmitting, by an array of acoustic wave transducers fixed on a bow centralizer on a tool used in a borehole or in a pipe located on a surface of Earth, acoustic waves, wherein each transducer in the array of acoustic wave transducers is configured to transmit acoustic waves at a given frequency different from frequencies of other transducers in the array of acoustic wave transducers;
receiving, by an array of acoustic wave receivers fixed on the bow centralizer on the tool used in the borehole or in a pipe located on the surface of Earth, the acoustic waves, wherein each receiver in the array of acoustic wave receivers is configured to receive only the given frequency of a given transducer, forming a receiver-transducer pair for the given frequency;

analyzing acoustic speeds measured at each given frequency and using different arrangements of acoustic wave transducers and acoustic wave receivers in the tool, including a transducer-responder-transducer arrangement; and generating a model, based on the analyzing, the model configured to predict fluid holdups along the borehole or the pipe and to perform fluid typing and fluid properties characterization in one phase, two phase, and three phase applications of gas, oil, and water.

2. The computer-implemented method of claim 1, wherein analyzing the acoustic speeds and generating the model includes:

using information from array production logs obtained using a spinner, the information used to determine flow rates of each fluid type;

using the model to estimate fluid type, density, and water salinity with known acoustic speeds of fluids at specific pressures and temperatures; and generating correlations and predictive charts using lab tests for each fluid type and holdup at different pressures, temperatures, and water salinities, wherein the correlations and predictive charts are configured to predict fluid holdups, densities, and salinities.

3. The computer-implemented method of claim 1, wherein the model includes one phase applications, including:

a single phase oil application modeling the condition of a single phase oil, using velocity (V), pressure (P), and temperature (T) measurements, and creating an output of oil density;

a single phase water application modeling the condition of a single phase water, using V, P, and T measurements, and creating an output of water salinity; and a single phase gas application modeling the condition of a single phase gas, using V, P, and T measurements, and creating an output of gas gravity.

4. The computer-implemented method of claim 1, wherein the model includes two phase applications, including:

a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity;

a double phase application modeling the condition of a horizontal wellbore with two phases including gas and water segregated by gravity; measurements T, P, and V for each set;

and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

5. The computer-implemented method of claim 1, wherein the model includes a three phase application, including:

a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

6. The computer-implemented method of claim 1, further comprising:

using the array of acoustic wave transducers and the array of acoustic wave receivers in a symmetrical compensated acoustic logging tool; and executing the symmetrical compensated acoustic logging tool at different transmitter/receiver arrangements and in different fluid flow directions.

7. The computer-implemented method of claim 1, further comprising plotting, in a graphical user interface, values determined using the model, wherein the values include salinity values, oil density values, and gas density values at different combinations of V, P, and T, wherein the values are plotted relative to an acoustic velocity axis, and wherein the values are annotated to indicate specific combinations of P and T.

8. A non-transitory, computer-readable medium storing one or more instructions executable by a computer system to perform operations comprising:

transmitting, by an array of acoustic wave transducers fixed on a bow centralizer on a tool used in a borehole or a pipe located on a surface of Earth, acoustic waves, wherein each transducer in the array of acoustic wave transducers is configured to transmit acoustic waves at a given frequency different from frequencies of other transducers in the array of acoustic wave transducers;

receiving, by an array of acoustic wave receivers fixed on the bow centralizer on the tool used in the borehole or a pipe located on the surface of Earth, the acoustic waves, wherein each receiver in the array of acoustic wave receivers is configured to receive only the given frequency of a given transducer, forming a receiver-transducer pair for the given frequency;

analyzing acoustic speeds measured at each given frequency and using different arrangements of acoustic wave transducers and acoustic wave receivers in the tool, including a transducer-responder-transducer arrangement; and generating a model, based on the analyzing, the model configured to predict fluid holdups along the borehole and to perform fluid typing and fluid properties characterization in one phase, two phase, and three phase applications of gas, oil, and water.

9. The non-transitory, computer-readable medium of claim 8, wherein analyzing the acoustic speeds and generating the model includes:

using information from array production logs obtained using a spinner, the information used to determine flow rates of each fluid type;

using the model to estimate fluid type, density, and water salinity with known acoustic speeds of fluids at specific pressures and temperatures; and generating correlations and predictive charts using lab tests for each fluid type and holdup at different pressures, temperatures, and water salinities, wherein the correlations and predictive charts are configured to predict fluid holdups, densities, and salinities.

10. The non-transitory, computer-readable medium of claim 8, wherein the model includes one phase applications, including:

a single phase oil application modeling the condition of a single phase oil, using velocity (V), pressure (P), and temperature (T) measurements, and creating an output of oil density;

a single phase water application modeling the condition of a single phase water, using V, P, and T measurements, and creating an output of water salinity; and a single phase gas application modeling the condition of a single phase gas, using V, P, and T measurements, and creating an output of gas gravity.

11. The non-transitory, computer-readable medium of claim 8, wherein the model includes two phase applications, including:

a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity;

a double phase application modeling the condition of a horizontal wellbore with two phases including gas and water segregated by gravity; measurements T, P, and V for each set; and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

12. The non-transitory, computer-readable medium of claim 8, wherein the model includes a three phase application, including:

a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

13. The non-transitory, computer-readable medium of claim 8, the operations further comprising:

using the array of acoustic wave transducers and the array of acoustic wave receivers in a symmetrical compensated acoustic logging tool; and executing the symmetrical compensated acoustic logging tool at different transmitter/receiver arrangements and in different fluid flow directions.

14. The non-transitory, computer-readable medium of claim 8, the operations further comprising plotting, in a graphical user interface, values determined using the model, wherein the values include salinity values, oil density values, and gas density values at different combinations of V, P, and T, wherein the values are plotted relative to an acoustic velocity axis, and wherein the values are annotated to indicate specific combinations of P and T.

15. A computer-implemented system, comprising:
one or more processors; and
a non-transitory computer-readable storage medium coupled to the one or more processors and storing programming instructions for execution by the one or more processors, the programming instructions instructing the one or more processors to perform operations comprising:

transmitting, by an array of acoustic wave transducers fixed on a bow centralizer on a tool used in a borehole or a pipe located on a surface of Earth, acoustic waves, wherein each transducer in the array of acoustic wave transducers is configured to transmit acoustic waves at a given frequency different from frequencies of other transducers in the array of acoustic wave transducers;

receiving, by an array of acoustic wave receivers fixed on the bow centralizer on the tool used in the borehole or a pipe located on the surface of Earth, the acoustic waves, wherein each receiver in the array of acoustic wave receivers is configured to receive only the given frequency of a given transducer, forming a receiver-transducer pair for the given frequency;

analyzing acoustic speeds measured at each given frequency and using different arrangements of acoustic wave transducers and acoustic wave receivers in the tool, including a transducer-responder-transducer arrangement, and generating a model, based on the analyzing, the model configured to predict fluid holdups across the borehole and to perform fluid typing and fluid properties characterization in one phase, two phase, and three phase applications of gas, oil, and water.

16. The computer-implemented system of claim 15, wherein analyzing the acoustic speeds and generating the model includes:

using information from array production logs obtained using a spinner, the information used to determine flow rates of each fluid type;

using the model to estimate fluid type, density, and water salinity with known acoustic speeds of fluids at specific pressures and temperatures; and generating correlations and predictive charts using lab tests for each fluid type and holdup at different pressures, temperatures, and water salinities, wherein the correlations and predictive charts are configured to predict fluid holdups, densities, and salinities.

17. The computer-implemented system of claim 15, wherein the model includes one phase applications, including:

a single phase oil application modeling the condition of a single phase oil, using velocity (V), pressure (P), and temperature (T) measurements, and creating an output of oil density;

a single phase water application modeling the condition of a single phase water, using V, P, and T measurements, and creating an output of water salinity; and a single phase gas application modeling the condition of a single phase gas, using V, P, and T measurements, and creating an output of gas gravity.

18. The computer-implemented system of claim 15, wherein the model includes two phase applications, including:

a double phase application modeling the condition of a horizontal wellbore with two phases including oil and water segregated by gravity; measurements T, P, and V for each set including a pair of a transmitter/transducer and a receiver; and an output of fluid holdup including oil/water for each set, oil density, and water salinity;

a double phase application modeling the condition of a horizontal wellbore with two phases including gas and water segregated by gravity; measurements T, P, and V for each set;

and an output including fluid holdup for gas/water for each set, gas gravity, and water salinity; and a double phase application modeling the condition of a horizontal wellbore with two phases including gas and oil segregated by gravity; measurements T, P, and V for each set; and an output of fluid holdup for gas/oil for each set, oil density, and gas gravity.

19. The computer-implemented system of claim 15, wherein the model includes a three phase application, including:
a triple phase application modeling the condition of horizontal wellbore with three phases including gas, oil, and water separated by gravity; measurements T, P, and V for each set; and an output including fluid holdup for gas/oil/water for each set, oil density, gas gravity, and water salinity.

20. The computer-implemented system of claim 15, the operations further comprising:
using the array of acoustic wave transducers and the array of acoustic wave receivers in a symmetrical compensated acoustic logging tool; and
executing the symmetrical compensated acoustic logging tool at different transmitter/receiver arrangements and in different fluid flow directions.

* * * * *